United States Patent [19]
Yamamoto et al.

[11] Patent Number: 5,332,731
[45] Date of Patent: Jul. 26, 1994

[54] CEPHALOSPORIN DERIVATIVES

[75] Inventors: Yuichi Yamamoto; Tsuneo Okonogi; Seiji Shibahara; Shigeharu Inoue, all of Yokohama, Japan

[73] Assignee: Meiji Seika Kaisha, Ltd., Japan

[21] Appl. No.: 623,215

[22] Filed: Dec. 6, 1990

[30] Foreign Application Priority Data

Dec. 7, 1989 [JP] Japan .................. 1-316423

[51] Int. Cl.⁵ .......................... C07D 501/36
[52] U.S. Cl. .................. 514/206; 540/226; 540/227
[58] Field of Search ............. 540/222, 227; 514/206

[56] References Cited
U.S. PATENT DOCUMENTS

| | | | |
|---|---|---|---|
| 4,256,739 | 3/1981 | Woodward et al. | 540/226 |
| 4,729,991 | 3/1988 | Veda et al. | 514/206 |
| 4,760,060 | 7/1988 | Mochida et al. | 514/210 |
| 4,812,562 | 3/1989 | Watanabe et al. | 540/227 |
| 5,239,068 | 8/1993 | Blaszczak et al. | 540/227 |
| 5,246,926 | 9/1993 | Bateson et al. | 514/202 |

FOREIGN PATENT DOCUMENTS 0009008 of 1980 Japan .
0182301 of 1986 Japan .
0210078 of 1987 Japan .

OTHER PUBLICATIONS

Chemical Abstracts vol. 115:182946m (1992).
Chem. Abstracts, 1991, vol. 114, No. 3, Jan. 21, 1991.

Primary Examiner—Nicholas S. Rizzo
Attorney, Agent, or Firm—Larson and Taylor

[57] ABSTRACT

A new class of cephalosporin derivatives is provided, which is useful as antibacterial agent to be particularly suitable for oral administrations in mammals including man, and which is represented by general formula (I)

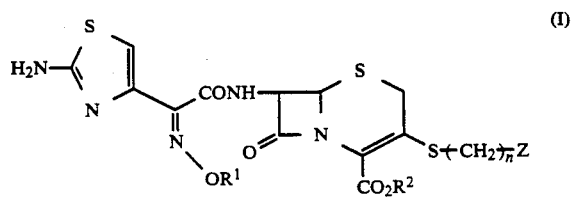

wherein $R^1$ is a hydrogen atom or a lower alkyl group; $R^2$ is a hydrogen atom or an ester-forming group capable of being cleaved easily with an esterase existing in the digestive tracts; n is an integer of zero or 1; Z is a saturated heterocyclic group containing one or two oxygen atoms as the hetero-atoms with or without one or more lower alkyl substituents, or a pharmaceutically acceptable salt thereof.

5 Claims, No Drawings

CEPHALOSPORIN DERIVATIVES

FIELD OF THE INVENTION

This invention relates to a new class of cephalosporin derivatives which exhibit a strong antibacterial activity. This invention also relates to a process for the production of the new cephalosporin derivatives and pharmacological applications thereof as antibacterial agent, particularly suitable for oral administrations in mammals, including human.

BACKGROUND OF THE INVENTION

Antibiotics of cephalosporin type are known to be highly active against a variety of gram-positive and gram-negative bacteria with high safety for mammals, so that they have been used widely and effectively for the therapeutic treatments of infectious diseases in mammals including man. In recent years, many researches have been directed to develop new classes of cephalosporin antibiotics of such a type that the cephalosporin compounds contain an aminothiazolylacetyl group as the acyl group in the 7-acylamino side chain on the cephem nucleus because they have been considered as being particularly attractive in view of their high anti-bacterial activity and stability to β-lactamase.

It is known that a family of such cephem compounds having a phenylglycylamino group on the 7-position and a relatively small functional group on the 3-position of the cephem compound, e.g. hydrogen atom, a halogen atom, or a methyl group, an alkoxy group, alkoxymethyl group or alkylthio group, as represented by cephalexin, generally possess a high absorption capacity through digestive tracts of patient upon oral administration. However, the antibacterial activity of such cephem compounds orally administered is always much inferior, against gram-negative bacteria, inter alia, against gram-negative bacteria capable of producing β-lactamase, to that of such cephalosporin compounds which are normally given to patient by injective administration.

Recently, on the other hand, there have been developed as oral administration drugs new cephalosporin compounds of which the 7-acylamino group contains an aminothiazole group, which are presented in the form of an ester derivative of the 4-carboxyl group, and of which the ester-forming group is easily clearable with the action of esterase existing in the digestive tracts. These caphalosporin antibiotics of the aminothiazole type can exhibit higher antibacterial activities against gram-negative bacteria than that of cephalexin, but unfortunately have such drawbacks that their anti-bacterial activities against gram-positive bacteria are rather lowered and that their absorption through digestive tracts of patient upon oral administration is still not satisfactorily high.

We, the present inventors, have proceeded with our investigations with a view to solving the problems discussed above and now succeeded in synthesizing a a new class of cephalosporin derivatives represented by a general formula (I) given below and we have found that they have a broad antibacterial spectrum and a high absorption capacity upon oral administration, in combination.

SUMMARY OF THE INVENTION

According to a first aspect of this invention, therefore, there is provided a new class of cephalosporin derivatives represented by general formula (I):

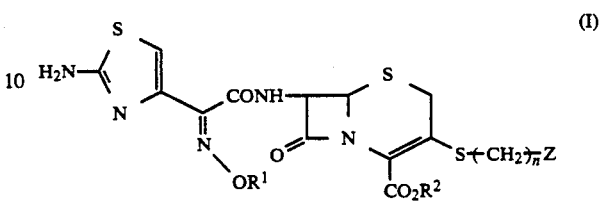

wherein $R^1$ is a hydrogen atom or a lower alkyl group; $R^2$ is a hydrogen atom or an ester-forming group capable of being cleaved easily with an esterase existing in the digestive tracts; is an integer of zero or 1; Z is a saturated heterocyclic group containing one or two oxygen atoms as the hetero-atoms with or without one or more lower alkyl substituents, or a pharmaceutically acceptable salt thereof.

A process for the preparation of cephalosporin derivatives of the general formula (I) comprising five steps or two steps hereinafter given constitutes another aspects of this invention, and an orally administrable pharmaceutical, antibacterial composition comprising a cephalosporin derivative of the general formula (I) as active ingredient constitutes a further aspect of this invention.

DETAILED DESCRIPTION OF THE INVENTION

In the general formula (I) which represents the new cephalosporin derivative according to the first aspect of this invention, the term "a lower alkyl group" for $R^1$ includes straight and branched alkyl groups containing 1 to 4 carbon atoms, for example, methyl, ethyl, a propyl and a butyl group.

The ester-forming group given for $R^2$ may be any of those which can be eliminated or cleaved from the 4-carboxyl group of the compounds of the general formula (I) by hydrolysis in vivo after the administration of said compounds. Exemplary of such ester-forming groups are a 1-acyloxy-lower alkyl group such as pivaloyloxymethyl, acetoxymethyl and 1-acetoxyethyl groups, etc.; a 1-alkoxycarbonyloxy-lower alkyl group such as 1-ethoxycarbonyloxyethyl and 1-isopropoxycarbonyloxyethyl groups, etc., and (5-methyl-2-oxo-1,3-dioxol-4-yl) methyl group, etc.

The saturated heterocyclic group for Z includes saturated 5-and 6-membered heterocyclic groups containing one or two oxygen atoms as the hetero atoms. Typical examples of such heterocyclic rings are tetrahydrofuran, tetrahydropyran, 1,3-dioxolane, 1,3-dioxane and 1,4-dioxane rings, and the like. These heterocyclic groups may be substituted by one or more lower alkyl group(s) containing up to 4 carbon atoms. The number and the position of the alkyl substituents on the heterocyclic group are not critical.

According to a prepared embodiment of the first aspect of this invention, therefore, the cephalosporin derivatives have a general formula (Ia):

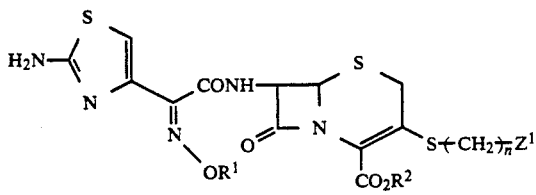

wherein $Z^1$ is a tetrahydrofuranyl, tetrahydropyranyl, 1,3-dioxolanyl or 1,3-dioxanyl group which may be substituted by one or more lower alkyl groups; $R^1$ and $R^2$ have the meanings as defined above; and n is zero or 1.

Typical examples of $Z^1$ are tetrahydrofuran-2-yl, tetrahydrofuran-3-yl, tetrahydropyran-2-yl, tetrahydropyran-4-yl, 1,3-dioxolan-4-yl, 2,2-dimethyl-1,3-dioxolan-4-yl, 1,3-dioxan-5-yl and 2,2-dimethyl-1,3-dioxan-4-yl groups. $R^1$ is preferred to be a hydrogen atom or methyl group.

Compounds of general formula (I) according to this invention may typically include, but are not limited to, the following particular compounds:

1. 7-[(Z)-2-(2-aminothiazol-4-yl)-2-methoxyiminoacetamido]-3-tetrahydrofurfurylthio-3-cephem-4-carboxylic acid (Compound No. 1);
2. pivaloyloxymethyl 7-[(Z)-2-(2-aminothiazol-4-yl)-2-methoxyiminoacetamido]-3-tetrahydrofurfurylthio-3-cephem-4-carboxylate (Compound No. 2);
3. 7-[(Z)-2-(2-aminothiazol-4-yl)-2-methoxyiminoacetamido]-3-(tetrahydrofuran-3-yl)thio-3-cephem-4-carboxylic acid (Compound No. 3);
4. pivaloyloxymethyl 7-[(Z)-2-(2-aminothiazol-4-yl)-2-methoxyiminoacetamido]-3-(tetrahydrofuran-3-Yl)thio-3-cephem-4-carboxylate (Compound No. 4);
5. 7-[(Z)-2-(2-aminothiazol-4-yl)-2-methoxyiminoacetamido]-3-(2,2-dimethyl-1,3-dioxolan-4-yl)methylthio-3-cephem-4-carboxylic acid (Compound No. 5);
6. pivaloyloxymethyl 7-[(Z)-2-(2-aminothiazol-4-yl)-2-methoxyiminoacetamido]-3-(2,2-dimethyl-1,3-dioxolan- 4-yl) methylthio-3-cephem-4-carboxylate (Compound No. 6);
7. 7-[(Z)-2-(2-aminothiazol-4-yl)-2-methoxyiminoacetamido]-3-(tetrahydropyran-4-yl)thio-3-cephem-4-carboxylic acid (Compound No. 7);
8. pivaloyloxymethyl 7-[(Z)-(2-aminothiazol-4-yl)-2-methoxyiminoacetamido]-3-(tetrahydropyran-4-yl) thio-3-cephem-4-carboxylate (Compound No. 8);
9. 7-[(Z)-2-(2-aminothiazol-4-yl)-2 -methoxyiminoacetamido]-3-(2,2-dimethyl-1,3-dioxan-4-yl)methylthio-3-cephem-4-carboxylic acid (Compound No. 9);
10. pivaloyloxymethyl 7-[(Z) -2-(2-aminothiazol-4-yl)-2-methoxyiminoacetamido]-3-(2,2-dimethyl-1,3-dioxan-4-yl)methylthio-3 -cephem-4-carboxylate (Compound No. 10);
11. 7-[(Z)-2-(2-aminothiazol-4-yl)-2-hydroxyiminoacetamido]-3-tetrahydrofurfurylthio-3-cephem-4-carboxylic acid (Compound No. 11);
12. pivaloyloxymethyl 7-[(Z)-2-(2-aminothiazol-4-yl)-2-hydroxyiminoacetamido]-3-tetrahydrofurfurylthio-3-cephem-4-carboxylate (Compound No. 12);
13. 7 -[(Z)-2-(2-aminothiazol-4-yl)-2-hydroxyiminoacetamido]-3-(tetrahydrofuran-3 -yl)thio-3-cephem-4-carboxylic acid (Compound No. 13);
14. pivaloyloxymethyl 7-[(Z)-2-(2-aminothiazol-4-yl)-2-hydroxyiminoacetamido]-3-(tetrahydrofuran-3-yl)thio-3-cephem-4-carboxylate (Compound No. 14);
15. 7- [(Z)-2-(2-aminothiazol-4-yl) -2-hydroxyiminoacetamido]-3 -(tetrahydropyran-4 -yl)thio-3-cephem-4-carboxylic acid (Compound No. 15);
16. pivaloyloxymethyl 7-[(Z)-2-(2-aminothiazol-4-yl)-2-hydroxyiminoacetamido]-3-(tetrahydropyran-4-yl) thio-3-cephem-4-carboxylate (Compound No. 16);
17. 7 - [(Z)-2-(2-aminothiazol-4 -yl) -2-hydroxyiminoacetamido]-3-(2,2-dimethyl-1,3-dioxan-4-yl)methylthio-3-cephem-4-carboxylic acid (Compound No. 17 );
18. pivaloyloxymethyl 7-[(Z)-2-(2-aminothiazol-4-yl)-2-hydroxyiminoacetamido]-3-(2,2-dimethyl-1,3-dioxan-4-yl) methylthio-3-cephem-4-carboxylate (Compound No. 18);
19. 7-[(Z)-2-(2-aminothiazol-4-yl)-2-methoxyiminoacetamido]-3-(1,3-dioxan-5-yl)thio-3-cephem-4-carboxylic acid (Compound No. 19);
20. pivaloyloxymethyl 7-[(Z)-2-(2-aminothiazol-4-yl)-2-methoxyiminoacetamido]-3-(1,3-dioxan-5-yl) thio-3-cephem-4-carboxylate (Compound No. 20);
21. 7 - [(Z) -2 -(2-aminothiazol-4 -yl) -2 -hydroxyiminoacetamido]-3-(1,3-dioxan-5-yl)thio-3-cephem-4-carboxylic acid (Compound No. 21);
22. pivaloyloxymethyl 7-[(Z)-2-(2-aminothiazol-4 -yl)-2-hydroxyiminoacetamido]-3-(1,3-dioxan-5-yl)thio-3-cephem-4-carboxylate (Compound No. 22);
23. 7-[(Z)-2-(2-aminothiazol-4-yl)-2-methoxyiminoacetamido]-3-(tetrahydropyran-2-yl)methylthio-3-cephem-4-carboxylic acid (Compound No. 23);
24. pivaloyloxymethyl 7-[(Z)-2-(2-aminothiazol-4-yl)-2-methoxyiminoacetamido]-3-(tetrahydropyran-2-yl) methylthio-3-cephem-4-carboxylate (Compound No. 24);
25. 7-[(Z)-2-(2-aminothiazol-4-yl)-2-hydroxyiminoacetamido]-3-(tetrahydropyran-2-yl)methylthio-3-cephem-4-carboxylic acid (Compound No. 25);
26. pivaloyloxymethyl 7-[(Z)-2-(2-aminothiazol-4-yl)-2-hydroxyiminoacetamido]-3-(tetrahydropyran-2-yl) methylthio-3-cephem-4-carboxylate (Compound No. 26).
27. 7-[(Z)-2-(2-aminothiazol-4-yl)-2-methoxyiminoacetamido]-3-(tetrahydrofuran-3-yl)methylthio-3-cephem-4-carboxylic acid (Compound No. 27);
28. pivaloyloxymethyl 7-[(Z)-2-(2-aminothiazol-4-yl)-2-methoxyiminoacetamido]-3-(tetrahydrofuran-3-yl) methylthio-3-cephem-4-carboxylate (Compound No. 28);
29. 7 - [(Z)-2-(2 -aminothiazol-4-yl)-2-methoxyiminoacetamido]-3-(1,3-dioxolan-4-yl)methylthio-3-cephem-4-carboxylic acid (Compound No. 29);
30. pivaloyloxymethyl 7-[(Z)-2-(2-aminothiazol-4-yl)-2-methoxyiminoacetamido]-3-(1,3-dioxolan-4-yl) methylthio-3-cephem-4-carboxylate (Compound No. 30);
31. 7-[(Z)-2-(2-aminothiazol-4-yl)-2-methoxyiminoacetamido]-3-(tetrahydropyran-4-yl)methylthio-3-cephem-4-carboxylic acid (Compound No. 31);
32. pivaloyloxymethyl 7-[(Z)-2-(2-aminothiazol-4-yl)-2-methoxyiminoacetamido]-3-(tetrahydropyran-4-yl) methylthio-3-cephem-4-carboxylate (Compound No. 32);

33. 7-[(Z)-2-(2-aminothiazol-4-yl)-2-methoxyiminoacetamido]-3-(1,3-dioxan-5-yl)methylthio-3-cephem-4-carboxylic acid (Compound No. 33);

34. pivaloyloxymethyl 7-[(Z)-2-(2-aminothiazol-4-yl)-2-methoxyiminoacetamido]-3-(1,3-dioxan-5-yl) methylthio-3-cephem-4-carboxylate (Compound No. 34);

35. 7-[(Z)-2-(2-aminothiazol-4-yl)-2-hydroxyiminoacetamido]-3-(1,3-dioxan-4-yl)methylthio-3-cephem-4-carboxylic acid (Compound No. 35);

36. pivaloyloxymethyl 7-[(Z)-2-(2-aminothiazol-4-yl)-2-hydroxyiminoacetamido]-3-(1,3-dioxan-4-yl)methylthio-3-cephem-4-carboxylate (Compound No. 36).

37. 7-[(Z)-2-(2-aminothiazol-4-yl)-2-hydroxyiminoacetamido]-3-(tetrahydropyran-4-yl)methylthio-3-cephem-4-carboxylic acid (Compound No. 37);

38. pivaloyloxymethyl 7-[(Z)-2-(2-aminothiazol-4-yl)-2-hydroxyiminoacetamido]-3-(tetrahydropyran-4-yl) methylthio-3-cephem-4-carboxylate (Compound No. 38);

Compound Nos. 1 to 38 mentioned above will be referred to hereinafter in Tests of determining the antibacterial activities and the recovery rate in urine of the above-mentioned particular compounds, for identifying these respective compounds.

Among the above mentioned examples of the cephalosporin derivative of general formula (I) according to this invention, particular compounds listed below are preferred:

(i) 7-[(Z)-2-(2-aminothiazol-4-yl)-2-methoxyiminoacetamido]-3-(tetrahydrofuran-3-yl)thio-3-cephem-4-carboxylic acid (Compound No. 3); its sodium salt (carboxylate) and its pivaloyloxymethyl ester.

(ii) 7-[(Z)-2-(2-aminothiazol-4-yl)-2-methoxyiminoacetamido]-3-(tetrahydrofuran-3-yl)methylthio-3-cephem-4-carboxylic acid (Compound No. 27); its sodium salt (carboxylate) and its pivaloyloxymethyl ester.

(iii) 7-[(Z)-2-(2-aminothiazol-4-yl)-2-methoxyiminoacetamido]-3-(1,3-dioxolan-4-yl)methylthio-3-cephem-4-carboxylic acid (Compound 29); its sodium salt (carboxylate) and its pivaloyloxymethyl ester.

The cephalosporin derivatives of general formula (I) according to this invention may be prepared by various processes. A convenient route for the preparation of the compounds of formula (I) comprises the following succesive steps (1)–(5) depicted below:

Step (1)

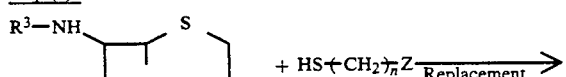

Compound (A1)     Compound (A2)

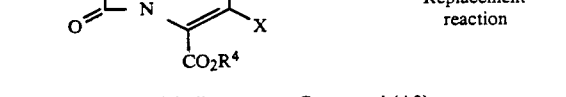

Compound (A3)

Step (2)

Compound (A3) + $\xrightarrow{\text{Deprotection reaction}}$

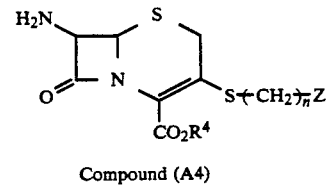

Compound (A4)

Step (3)

Compound (A4) +

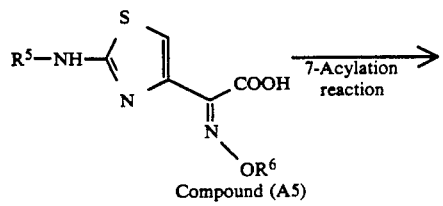

Compound (A5)

$\xrightarrow{\text{7-Acylation reaction}}$

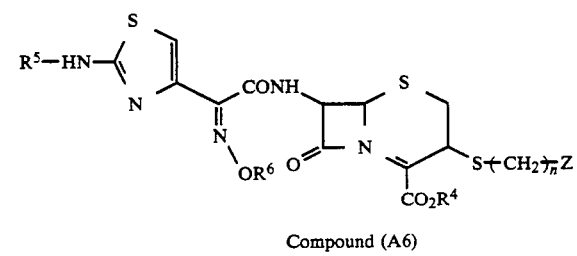

Compound (A6)

Step (4)

Compound (A6) $\xrightarrow{\text{Deprotection reaction}}$

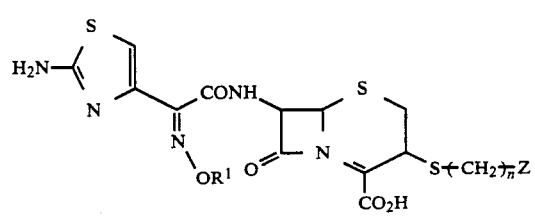

Compound (I') ($R^2$ = H)

Step (5)

Compound (I') + $R^2OH$ $\xrightarrow{\text{Esterification reaction}}$

Compound (A7)

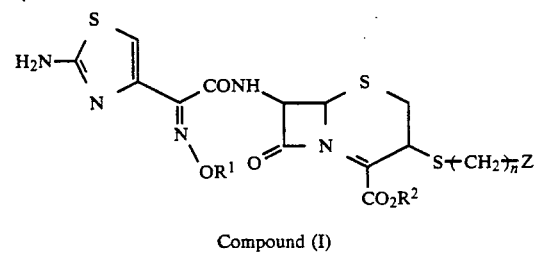

Compound (I)

In formulae (A1) to (A7) and (I') given in the reaction scheme above, $R^1$, $R^2$, n and Z have the same meanings as defined in the formula (I).

In the starting compound (A1), $R^3$ represents an amino-protecting group such as phenylacetyl, phenoxyacetyl, 2-thienylacetyl, formyl, t-butoxycarbonyl groups and the like, and X represents a leaving group such as a halogen atom, or diphenylphosphoryloxy, methanesulfonyloxy and p-toluenesulfonyloxy groups, etc.

In the reactant compound (A5), $R^5$ represents an amino-protecting group such as trityl, chloroacetyl and formyl groups, etc.; and $R^6$ represents a lower alkyl group or $R^6$ represents an oxime-protecting group such as trityl group when $R^1$ is hydrogen atom.

Some details of the 5-step process shown in the reaction scheme as above are now explained.

Step (1) comprises conducting replacement reaction between the starting compound (A1) and the reactant compound (A2), i.e. a mercaptan compound having a hetero-ring (Z) desired, in an anhydrous solvent in the presence of a base so as to give the compound (A3) as the reaction product. As the anhydrous solvent, chloroform, dichloromethane, dimethylformamide, acetonitrile, hexamethylphosphoric triamide and the like are preferred. Preferred bases may be organic bases such as triethylamine, tributylamine, N,N-diisopropylethylamine, and the like. Reaction temperature used is preferably in the range of $-20°$ C. to $10°$ C. After the completion of the reaction, the reaction product is post-treated in a usual manner and, if necessary, purified by silica gel-column chromatography, etc. to obtain the desired compound (A3) in a high purity.

Step (2) comprises conducting the removal of the 7-amino-protecting group ($R^3$), typically the removal of a N-protecting acyl group on the 7-amino group, from compound (A3) for its deprotection to give 7-aminocephem compound (A4) having the free 7-amino group. The deprotection reaction may be effected in a manner used conventionally for the removal of such amino-protecting group as $R^3$. In case where $R^3$ is phenylacetyl, phenoxyacetyl or 2-thienylacetyl group, etc., a most conventional method for the deprotection used in the art, may be employed, and thus the reaction of the compound (A3) with phosphorus pentachloride in the presence of an organic base, and then with an alcohol, is preferred. The resulting deprotected compound (A4) may be purified by crystallization or verious chromatographic techniques to isolate the compound (4), or may be used directly, i.e. without being purified, for the next step, i.e. Step (3).

Step (3) comprises acylating the 7-amino group of the 7-aminocephem compound (A4) with a carboxylic acid compound (A5), i.e. an aminothiazolylacetic acid compound or an active derivative thereof as desired, in order to obtain compound (A6) as the reaction product. The acylation reaciton may be any of those usually employed in the peptide chemistry. For example, compound (A6) may be prepared by reacting compound (A4) with the aminothiazolylacetic acid compound (A5) or an active derivative thereof in the presence of a variety of condensing agents. Exemplary of the condensing agents are carbodiimides such as DCC, WSDCC; Vilsmeier reagent, phosphorus oxychloride and EEDQ. A particular condensing agent may appropriately be selected in each particular case by taking reactivities of particular reactant compounds (A4) and (A5) or active derivative thereof into consideration. The solvent used may, for example, be dichloromethane, chloroform, dimethylformamide, tetrahydrofuran, etc. The reaction temperature may be in the range of $-20°$ C. to $+50°$ C., preferably $-20°$ C. to $0°$ C. After the completion of the reaction, the reaction product (A6) may be post-treated in a usual manner and, if necessary, purified by silica gel-column chromatography, etc. to obtain the desired compound (A6) in a high purity.

Step (4) comprises effecting the deprotection, i.e. the removal of the residual protecting groups $R^4$, $R^5$ and $R^6$, of compound (A6) to give such a compound of general formula (I) wherein $R^2$ is a hydrogen atom, that is, a compound of general formula (I').

This deprotection reaction in Step (4) may be conducted in accordance with a usual method for the removal of the protecting groups $R^4$, $R^5$ and $R^6$ in accordance with the natures of these groups. If the deprotection is to be effected under an acidic condition, trifluoroacetic acid, formic acid, hydrochloric acid, etc. may be used, whereas a catalytic reduction using a variety of catalyst or an reduction with a metal such as zinc may be used if the deprotection is to be conducted under a reductive condition. In case where the amino-protecting group $R^5$ is chloroacetyl group, the reaction with a variety of thioamides can achieve the removal of this particular group. The compound of formula (I') thus obtained may be purified and isolated in a usual manner, for example, by crystallization or precipitation from an aqueous solution thereof by regulating the pH of the solution, by chromatography using a non-ionic macroporous resin and/or by gel filtration using a gel filler such as Sephadex (a product of Pharmacia Fine Chemical Co.).

Step (5) comprises an esterification step required for the preparation of compounds of general formula (I) wherein $R^2$ is an ester-forming group capable of being cleaved easily with an esterase existing in the digestive tracts. This step comprises esterifying compound (I') as obtained in Step (4) with an alcohol compound (A7) having a desired ester-forming group $R^2$, namely an alcohol of a formula $R^2OH$, or an activated derivative thereof, for example, its halogenated derivative of formula $R^2Hal$ where Hal denotes a bromine, iodine or chlorine atom, in a known manner. The esterification reaction may be conducted in a solvent at a temperature of $-40°$ C. to room temperature, preferably at $-20°$ C. to $0°$ C. As the solvent, acetonitrile, dimethylformamide, dimethylacetamide, acetone and the like are preferred. The time required for the reaction may vary depending upon the reactivity of the substrate compound (I'), quantity of the esterifying agent, reaction temperature, etc. and it usually is within one hour for the completion. After the completion of the reaciton, the reaction product as formed may be post-treated in a usual manner and, if necessary, purified by silica gel-column chromatography and the like, followed by precipitation or crystallization, whereby isolating the desired compound of formula (I) where $R^2$ is an ester-forming group.

According to a second aspect of this invention, therefore, there is provided a process for the preparation of a cephalosporin derivative of general formula (I) as defined hereinbefore, which comprises the steps of:

(1) reacting a compound of general formula (A1)

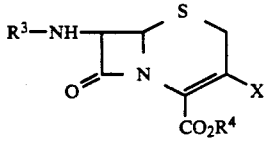
(A1)

wherein $R^3$ is an amino-protecting group; $R^4$ is a carboxylate ester-forming group as a carboxyl-protecting group; and X is a leaving group, with a mercaptan compound of general formula (A2)

(A2)

wherein Z and n have the meanings as defined hereinbefore to produce a compound of general formula (A3)

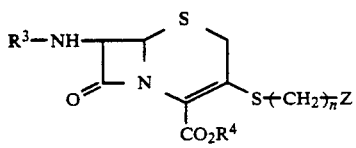
(A3)

wherein $R^3$, $R^4$, Z and n are as defined above,
(2) removing the 7-amino-protecting group $R^3$ of compound (A3) in a usual manner to produce a compound of general formula (A4)

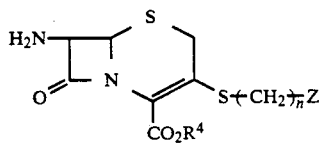
(A4)

wherein $R^4$, Z and n are as defined above,
(3) acylating the resulting compound (A4) at its 7-amino group with an aminothiazolylacetic acid compound of general formula (A5)

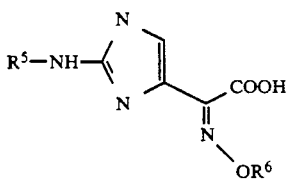
(A5)

wherein $R^5$ is an amino-protecting group; and $R^6$ is a lower alkyl group or is an oxime-protecting group when $R^1$ of the final compound (I) is a hydrogen atom, to produce a compound of general formula (A6)

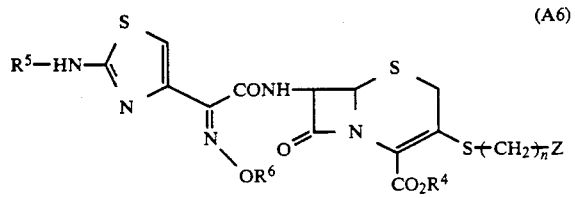
(A6)

wherein $R^4$, $R^5$, $R^6$, Z and n are as defined above, (4) removing the carboxyl-protecting group $R^4$, the amino-protecting group $R^5$ and the hydroxyl-protecting group $R^6$ of compound (A6) in usual manner to produce a compound (I) where $R^2$ is a hydrogen atom; and, if necessary, (5) esterifying the resulting compound (I) where $R^2$ is hydrogen atom with an alcohol compound of general formula (A7)

$R^2OH$ (A7)

wherein $R^2$ is an ester-forming group capable of being cleaved easily with an esterase existing in the digestive tracts or an activated derivative of the alcohol (A7), to produce a compound of the formula (I) wherein $R^2$ is an ester-forming group defined above.

According to a third aspect of this invention as a particular embodiment of the second aspect process of this invention, there is provided a process for the preparation of a cephalosporin derivative of general formula (I) as defined hereinbefore, which comprises the steps of:

(i) acylating the 7-amino group of the compound of general formula (A4)

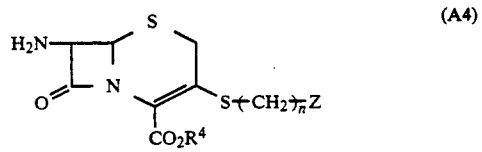
(A4)

wherein $R^4$ is a carboxylate ester-forming group, and Z and n are as defined hereinbefore, with an aminothiazolylacetic acid compound of general formula (A5)

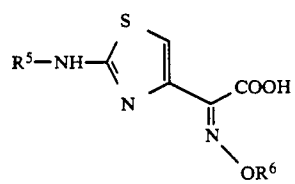
(A5)

wherein $R^5$ is an amino-protecting group; and $R^6$ is a lower alkyl group or is an oxime-protecting group when $R^1$ of the final compound of formula (I) is hydrogen atom, to produce a compound of general formula (A6)

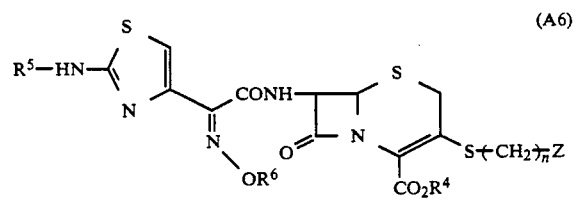
(A6)

wherein $R^4$, $R^5$, $R^6$, Z and n are as defined above, (ii) removing the carboxyl-protecting group $R^4$, the amino-protecting group $R^5$ and the hydroxyl-protecting group $R^6$ of compound (A6) in usual manner to produce a compound of formula (I) where $R^2$ is a hydrogen atom; and, if necessary, (iii) esterifying the resulting compound of formula (I) where $R^2$ is hydrogen atom with an alcohol compound of general formula (A7)

$$R^2OH \quad (A7)$$

wherein $R^2$ is an ester-forming group capable of being cleaved easily with an esterase existing in the digestive tracts or an activated derivative of the alcohol (A7), to produce a compound of formula (I) wherein $R^2$ is an ester-forming group defined above.

In the process according to the third aspect of this invention, the steps (i), (ii) and (iii) may be carried out entirely in the same manner as in the steps (3), (4) and (5) of the process of the second aspect of this invention, respectively.

Incidentally, the intermediate compounds (A3) and (A6) which were prepared in Step (1) and Step (3), respectively, of the reaction scheme above-mentioned for the preparation of the compounds of general formula (I) can also be prepared via other route. Thus, these intermediate compounds (A3) and (A6) can be prepared more easily by such an alternative, new process as described in copending Japanese Patent Application No. 316424/1989 relating to "A process for the preparation of 3-substituted thio-3-cephem compounds", wherein a certain 3-acylthiocephem compound is prepared as a starting compound and then converted to a 3-alkylthiocephem compound.

This alternative new process for preparing the intermediate compounds (A3) and (A6) comprises Steps (a), (b) and (c) briefly represented by the following schematic reaction equations:

Step (a)

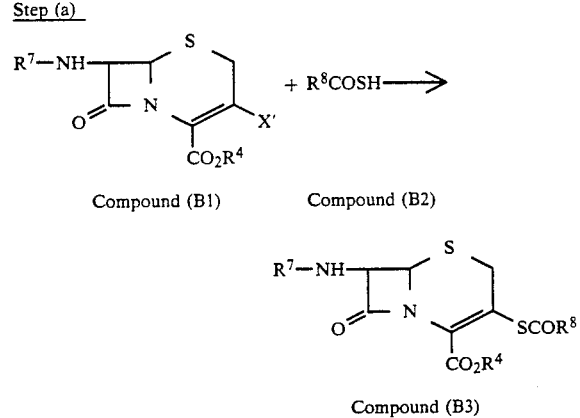

Compound (B1)   Compound (B2)

Compound (B3)

Step (b)

Compound (B3) + Tertiary amine + Secondary amine ⟶

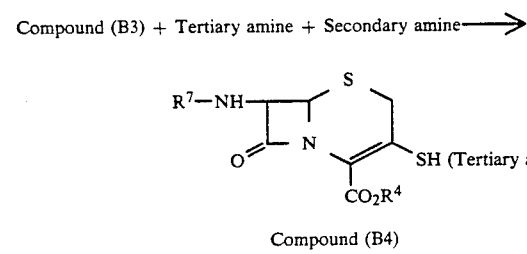

Compound (B4)

Step (c)

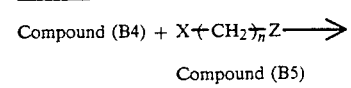

Compound (B5)

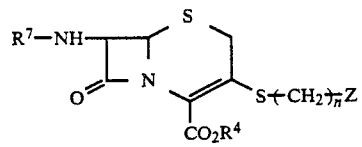

Compound (B6)

In the starting compound (B1) used in Step (a) of the reaction scheme above, group X' is a leaving group which may conveniently be diphenylphosphoryloxy or methanesulfonyloxy group; $R^4$ has the same meaning as defined hereinbefore; and $R^7$ is an acyl group, preferably phenylacetyl group.

In the reactant compound used in Step (a), i.e. a thio acid compound (B2), $R^8$ represents a lower alkyl group such as methyl, ethyl, etc. or an unsubstituted or substituted aryl group such as phenyl, p-methoxyphenyl, p-nitrophenyl, p-tolyl and the like.

In the heterocyclic compound (B5) or heterocyclic ring-containing compound used in Step (c), X, Z and n have the same meanings as defied hereinbefore.

In Step (a) above, compound (B1) is reacted with compound (B2), i.e. a thio acid compound of formula $R^8COSH$ in an anhydrous solvent in the presence of a base to give compound (B3) as the reaction product. The reaction may be carried out in the same manner as in Step (1) of the process above-mentioned for the preparation of compound (I) according to the second aspect of this invention. The thio acid compound (B2) and base may be used in excess amounts in respect of the amount of compound (B3). In each particular case, the amounts of the thio acid and base may depend upon the reactivities thereof to be used, usually 1 to 2 equivalents of the former and 2 to 4 equivalents of the latter are used for the reaction. The reaction temperature may preferably be $-20°$ C. to room temperature. After the completion of the reaction, the reaction product (B3) may be post-treated in a usual manner and, if necessary, purified by silica gel-column chromatography, etc.

In Step (b) above, the resulting compound (B3) is then reacted with a tertiary amine and secondary amine to give compound (B4) as a desired reaction product. Typical tertiary amines available for this purpose are trimethylamine, triethylamine, tributylamine, N,N-diisopropylethylamine, N-methylmorpholine and the like; and typical secondary amines are morpholine, pyrrolidine, piperidine, piperazine, diethylamine, and the like. Both the tertiary and secondary amines should necessarily be used at least 1.0 equivalent each in respect of the amount of compound (B3) used. The use of 1.0 to 1.1 equivalents each of the tertiary and secondary amines may be most suitable. Examples of suitable anhydrous solvents to be used may include polar solvents such as acetonitrile, dimethylsulfoxide, N,N-dimethylformamide, N,N-dimethylacetamide, N-methylpyrrolidone, etc.; dichloromethane; tetrahydrofuran, etc. The reaction temperature is not critical, but usually the reaction is preferably carried out under ice-cooling condition or at room temperatures. The reaction time may vary depending upon the nature of compound (B3) and the reaction conditions employed, but may usually be within one hour. The completion of the reaction may be confirmed by detecting the formation of the desired compound (B4) with thin-layer chromatography, etc., after which Step (c) is to be carried out.

In Step (c), compound (B4) is reacted with the heterocyclic compound (B5), whereby compound (B6) results from the replacement reaction involved. Compound (B6) so obtained as the reaction product corresponds to compound (A3) formed in Step (1) above if the group $R^7$ of compound (B6) is the same as $R^3$ of compound (A3), and corresponds to compound (A6) formed in Step (3) above if the group $R^7$ of compound (B6) is an aminothiazolylacetic acid derivative.

Compound (B5) used in Step (c), i.e. the heterocyclic compound represented by formula $Z-(CH_2)_n-X$ acts as a reagent for introduction of the group $-(CH_2)n-Z$ into the 3-thio group of Compound (B4), whereupon the replacement reaction takes place. The reagent compound (B5) may be used in an excess amount in respect of compound (B4) and preferably in an amount of 1.0 to 5.0 equivalents. The reaction temperature is not critical. Usually, the reaction may preferably be conducted under ice-cooling or at room temperature. The reaction time may vary depending upon the reactivities and quantities of the compound (B4) and the reagent (B5) used or the nature of solvent used and other reaction conditions, but may usually be within one hour. The reaction product desired, i.e. compound (B6) obtained in Step (c) may, if necessary, be purified and isolated in a usual manner, for example, by chromatographic techniques and crystallization.

The cephalosporin derivatives of general formula (I) according to this invention, we have confirmed, have high antibacterial activities against a variety of pathogenic bacteria and high absorption or uptake capacities upon oral administration. Therefore, they are useful as antibacterial agents particularly for oral administration in mammals, including man.

According to a further aspect of this invention, therefore, there is provided a pharmaceutical, antibacterial composition comprising an antibacterially effective amount of a compound of general formula (I) given hereinabove or a pharmaceutically acceptable salt thereof as active ingredient, in combination with a pharmaceutically acceptable carrier for the active ingredient.

The pharmaceutically acceptable carrier as mixed with the active ingredient compound may be an ordinary solid or liquid one, either organic or inorganic, for example, starch, sugar, water and aqueous ethanol, which may be chosen appropriately depending on whether the pharmaceutical formulation as prepared is to be administered orally or non-orally or applied externally. The pharmaceutical composition of this invention may be of any conventional formulation form such as capsules, tablets, sugar-coated pills, ointment, suppository, solution, suspension and emulsion. Other conventional additives, including adjuvant, stabilizing agent, wetting agent, emulsifying agent, buffer solution may also be incorporated into the pharmaceutical composition of this invention containing the compound of the formula (I) as the active ingredient.

The excellent antibacterial activity and high absorbability upon oral administration of the new cephalosporin compounds of general formula (I) will now be illustrated on some typical compounds in the following Test Examples.

TEST EXAMPLE 1

Antibacterial activity of Compounds Nos. 1, 3, 5, 7, 9, 11, 13, 15, 17, 19, 21, 23, 25, 27, 29, 31, 33, 35 and 37 indentified hereinbefore which are the particular examples of the new cephalosporin derivative of general formula (I) according to this invention and which are in the form of the free carboxylic acid was estimated by determining the minimum inhibitory concentrations (MIC., $\mu g/ml$) of these compounds against a variety of bacteria according to a standard serial dilution method. The results of the determination are shown as their antibacterial spectra in Table 1 below.

TABLE 1

| | MIC. ($\mu g/ml$) | | | | | | | | | | | |
|---|---|---|---|---|---|---|---|---|---|---|---|---|
| Test organisms | Compound No. 3 | Compound No. 13 | Compound No. 1 | Compound No. 11 | Compound No. 5 | Compound No. 7 | Compound No. 15 | Compound No. 9 | Compound No. 17 | Compound No. 19 | Compound No. 21 | Compound No. 23 |
| *Staphylococcus aureus* 209P JC-1 | 0.20 | 0.20 | 0.20 | 0.20 | 1.56 | 0.78 | 0.20 | 1.56 | 0.78 | 0.39 | 0.20 | 3.13 |
| *Staphylococcus epidermidis* ATCC14990 | 0.39 | 0.20 | 0.78 | 0.20 | 1.56 | 0.39 | 0.20 | 1.56 | 0.39 | 0.78 | 0.20 | 3.13 |
| *Enterobacter hirae* ATCC8043 | 12.5 | 3.13 | 12.5 | 6.25 | 25 | 6.25 | 6.25 | 25 | 25 | 25 | 3.13 | 25 |
| *Entrobacter faecalis* W-73 | >100 | 12.5 | 100 | 6.25 | 50 | >100 | 1.56 | 100 | 6.25 | 100 | 12.5 | >100 |
| *Escherichia coli* W3630 RGN823 | 0.78 | 1.56 | 1.56 | 1.56 | 1.56 | 1.56 | 12.5 | 1.56 | 6.25 | 0.78 | 3.13 | 3.13 |
| *Escherichia coli* NIHJ JC-2 | 0.39 | 0.39 | 1.56 | 1.56 | 1.56 | 0.78 | 0.78 | 3.13 | 6.25 | 0.39 | 0.20 | 3.13 |
| *Klebsiella pneumoniae* GN69 | 0.20 | 0.39 | 0.39 | 0.78 | 0.78 | 0.78 | 0.78 | 1.56 | 3.13 | 0.20 | 0.20 | 1.56 |
| *Klebsiella pneumoniae* PC1602 | 0.20 | 0.20 | 0.78 | 0.78 | 1.56 | 0.39 | 0.39 | 3.13 | 6.25 | <0.025 | 0.20 | 3.13 |
| *Escherichia coli* 255 | 50 | 50 | 25 | 50 | 100 | 50 | 50 | 100 | 100 | 25 | 25 | 50 |
| *Escherichia coli* 255/S-1 | 0.39 | 0.39 | 0.78 | 0.78 | 3.13 | 0.78 | 0.39 | 6.25 | 6.25 | 0.39 | 0.20 | 3.13 |
| *Escherichia coli* GN206 | 12.5 | 12.5 | 6.25 | 12.5 | 12.5 | 12.5 | 12.5 | 12.5 | 25 | 3.13 | 6.25 | 6.25 |
| *Proteus vulgaris* GN76 | 0.10 | 1.56 | 0.20 | 0.78 | 0.39 | 0.20 | 1.56 | 0.78 | 3.13 | 0.05 | 0.78 | 0.39 |
| *Proteus vulgaris* GN76/C-1 | 1.56 | 6.25 | 3.13 | 6.75 | 1.56 | 0.78 | 6.25 | 3.13 | 25 | 1.56 | 12.5 | 1.56 |
| *Marganella morganii* 1510 | 25 | 12.5 | 50 | 50 | 100 | 50 | 50 | 100 | >100 | 12.5 | 12.5 | 50 |
| *Marganella morganii* 1510/S-1 | 0.20 | 0.20 | 0.39 | 0.39 | 0.78 | 0.20 | 0.20 | 1.56 | 3.13 | 0.10 | 0.10 | 0.78 |
| *Citrobacter freundii* GN346 | >100 | >100 | >100 | >100 | >100 | >100 | >100 | >100 | >100 | >100 | >100 | >100 |
| *Citrobacter freundii* GN346/16 | 3.13 | 3.13 | 3.13 | 6.25 | 6.25 | 6.25 | 6.25 | 6.25 | 12.5 | 3.13 | 3.13 | 6.25 |
| *Enterobacter cloacae* GN7471 | 50 | 100 | 50 | 50 | 50 | 50 | 100 | 50 | >100 | 50 | 50 | 100 |
| *Enterobacter cloacae* G-0008 | 12.5 | 6.25 | 1.56 | 1.56 | 3.13 | 0.78 | 1.56 | 3.13 | 12.5 | 0.39 | 0.78 | 3.13 |
| *Serratia marcescens* GN10857 | 100 | >100 | 100 | >100 | 50 | 100 | >100 | 50 | >100 | 50 | >100 | 50 |
| *Serratia marcescens* No. 1 | 12.5 | 3.13 | 0.78 | 1.56 | 1.56 | 0.78 | 6.25 | 3.13 | 12.5 | 0.78 | 3.13 | 1.56 |
| *Pseudomonas aeruginosa* | >100 | >100 | >100 | >100 | >100 | >100 | >100 | >100 | >100 | >100 | >100 | 100 |

TABLE 1-continued

GN10362

| Test organisms | MIC. (μg/ml) | | | | | | |
|---|---|---|---|---|---|---|---|
| | Compound No. 25 | Compound No. 27 | Compound No. 29 | Compound No. 31 | Compound No. 33 | Compound No. 35 | Compound No. 37 |
| Staphylococcus aureus 209P JC-1 | 1.56 | 1.56 | 1.56 | 1.56 | 0.78 | 0.39 | 0.39 |
| Staphylococcus epidermidis ATCC14990 | 1.56 | 0.78 | 0.78 | 1.56 | 0.78 | 0.20 | 0.39 |
| Enterobacter hirae ATCC8043 | 12.5 | >100 | >100 | >100 | >100 | 12.5 | 50 |
| Entrobacter faecalis W-73 | 12.5 | 100 | >100 | >100 | >100 | 12.5 | 25 |
| Escherichia coli W3630 RGN823 | 12.5 | 0.78 | 0.78 | 1.56 | 0.78 | 1.56 | 6.25 |
| Escherichia coli NIHJ JC-2 | 12.5 | 0.78 | 0.39 | 1.56 | 0.78 | 0.39 | 3.13 |
| Klebsiella pneumoniae GN69 | 12.5 | 0.20 | 0.20 | 0.78 | 0.10 | 0.05 | 0.10 |
| Klebsiella pneumoniae PCI602 | 12.5 | 0.39 | 0.20 | 1.56 | 0.39 | 0.39 | 3.13 |
| Escherichia coli 255 | 100 | 50 | 50 | 25 | 50 | 50 | 50 |
| Escherichia coli 255/S-1 | 12.5 | 0.78 | 0.39 | 1.56 | 0.78 | 0.39 | 3.13 |
| Escherichia coli GN206 | 12.5 | 6.25 | 6.25 | 6.25 | 6.25 | 12.5 | 12.5 |
| Proteus vulgaris GN76 | 3.13 | 0.20 | 0.10 | 0.78 | 0.20 | 12.5 | 3.13 |
| Proteus vulgaris GN76/C-1 | 12.5 | 6.25 | 6.25 | 12.5 | 6.25 | 100 | 50 |
| Marganella morganii 1510 | 100 | 25 | 50 | 100 | 100 | 50 | 100 |
| Marganella morganii 1510/S-1 | 0.78 | 0.39 | 0.39 | 0.78 | 0.39 | 0.20 | 0.78 |
| Citrobacter freundii GN346 | >100 | >100 | >100 | >100 | >100 | >100 | >100 |
| Citrobacter freundii GN346/16 | 12.5 | 3.13 | 3.13 | 3.13 | 3.13 | 3.13 | 6.25 |
| Enterobacter cloacae GN7471 | 100 | 50 | 50 | 50 | 50 | 50 | 100 |
| Enterobacter cloacae G-0008 | 25 | 0.78 | 0.39 | 1.56 | 0.78 | 1.56 | 3.13 |
| Serratia marcescens GN10857 | >100 | 50 | 50 | 25 | 50 | >100 | >100 |
| Serratia marcescens No. 1 | 6.25 | 3.13 | 3.13 | 3.13 | 0.78 | 12.5 | 12.5 |
| Pseudomonas aeruginosa GN10362 | >100 | >100 | >100 | 100 | >100 | >100 | >100 |

With regard to Table 1 above, it may be noted that Compounds Nos. 3, 13, 1, 11, 5, 7, 15, 9, 17, 19, 21, 23, 25, 27, 29, 31, 33, 35 and 37 indicated in Table 1 are corresponding to the compounds nominated in Example 1(e), Example 3(b), Example 5(d), Example 7(b), Example 9(c), Example 11(d), Example 13(b), Example 15(b) Example 17(c), Example 19(b), Example 21(b), Example 23(d), Example 25(b), Example 27(c), Example 29(b), Example 31(b), Example 33(b), Example 35(b), Example 37(b), given hereinafter, respectively.

TEST EXAMPLE 2

The fact that the new cephalosporin compound of this invention as orally administered is easily absorbed or up-taken through digestive tract by a living animal and maintains its antibacterial activity to a substantial extent in the body of animal until it is excreted in the urine of the animal can be demonstrated by determining the remaining amount of the active cephalosporin compound which can be recovered in the urine in the form of its free carboxylic acid. Thus, some tests were made to evaluate the amount or rate of the cephalosporin compound of this invention which can be recovered as the antibacterially active compound from the urine after it was orally given to mice.

The test compounds estimated in this test for their rate of recovery from urine are Compounds Nos. 2, 4, 6, 8, 10, 12, 14, 16, 18, 20, 22, 24, 26, 28, 30, 32, 34, 36 and 38 identified hereinbefore which are the particular examples of the cephalosporin derivative of general formula (I) of this invention and which are in the form of the pivaloyloxymethyl ester.

TEST METHOD

To mice of ICR-strain (male, 4-weeks-aged, five mice in each group) was orally administered the test compound identified above at a dosage of 0.5 mg per mouse. By the end of 4 hours after the administration of the test compound, all the amounts of the urine excreted by the treated mice were collected together, and the total quantity of the cephalosporin compound of this invention (as the free carboxylic acid form) in the urine so collected was determined according to a paper-disc assay method using *Escherichia coli* K-12 8236 strain as the assay strain.

Rate of recovery of the cephalosporin compound in urine was calculated in terms of percentage of the molar quantity of the cephalosporin compound as recovered (as the free carboxylic acid form) against the molor quantity of the cephalosporin compound as orally administered.

TEST RESULTS

The test results obtained (as averaged) are shown in Table 2.

TABLE 2

| Test Compound | Rate of recovery of test compound remaining in urine collected during 0 to 4 hours after oral administration, (%) |
|---|---|
| Compound No. 4 | 30.3 |
| Compound No. 14 | 24.7 |
| Compound No. 2 | 18.1 |
| Compound No. 12 | 13.0 |
| Compound No. 6 | 23.2 |
| Compound No. 8 | 27.3 |
| Compound No. 16 | 13.9 |
| Compound No. 10 | 18.5 |

TABLE 2-continued

| Test Compound | Rate of recovery of test compound remaining in urine collected during 0 to 4 hours after oral administration, (%) |
|---|---|
| Compound No. 18 | 5.4 |
| Compound No. 20 | 5.7 |
| Compound No. 22 | 3.9 |
| Compound No. 24 | 11.9 |
| Compound No. 26 | 18.1 |
| Compound No. 28 | 29.1 |
| Compound No. 30 | 41.3 |
| Compound No. 32 | 17.4 |
| Compound No. 34 | 19.8 |
| Compound No. 36 | 12.9 |
| Compound No. 38 | Less than detectable amount |

With regard to Table 2 above, it may be noted that Compounds Nos. 4, 14, 2, 12, 6, 8, 16, 10, 18, 20, 22, 24, 26, 28, 30, 32, 34, 36 and 38 indicated in Table 2 are corresponding to the compounds nominated in Example 2, Example 4, Example 6, Example 8, Example 10, Example 12, Example 14, Example 16, Example 18, Example 20, Example 22, Example 24, Example 26, Example 28, Example 30, Example 32, Example 34, Example 36 and Example 38 given hereinafter, respectively.

The cephalosporin derivative of general formula (I) according to this invention can safely be administered to mammals because it is of low toxicity, as demonstrated by the fact that mice could tolerate oral administration of pivaloyloxymethyl ester of 7-[(Z)-2-(2-aminothiazol-4-yl)-2-methoxyiminoacetamido]-3-(tetrahydrofuran-3-yl) thio-3-cephem-4-carboxylic acid; 7-[(Z)-2-(2-aminothiazol-4-yl)-2-methoxyiminoacetamido]-3-(tetrahydrofuran-3-yl) methylthio-3-cephem-4-carboxylic acid; or 7-[(Z)-2-(2-aminothiazol-4-yl)-2-methoxyiminoacetamido]-3-(1,3-dioxolan-4-yl)methylthio-3-cephem-4-carboxylic acid at a dosage of 3 g/kg without exhibiting toxic symptoms. The new cephalosporin derivative of this invention may be administered orally at a unit dose of 100 mg to 250 mg to an adult human patient four times a day, for a guideline. However, precise dosage of the new cephalosporin is determinable through preliminary routine experiments, depending on the body weight, ages, sex and other various parameters of patients as well as the nature of the bacterial infections to be treated, and so on.

The following Examples further illustrate the preparation and identification of the cephalosporin derivatives of this invention, but are not to be construed as limiting the invention thereto.

EXAMPLE 1

Preparation of
7-[(Z)-2-(2-aminothiazol-4-yl)-2-methoxyiminoacetamido]-3-(tetrahydrofuran-3-yl)thio-3-cephem-4-carboxylic acid (a) Tetrahydrofuran-3-yl Trifluoromethanesulfonate 3-Hydroxytetrahydrofuran (441 mg) and pyridine (0.49 ml) were dissolved in dichloromethane (4 ml) and the resulting solution was cooled to $-50°$ C. Trifluoromethanesulfonic acid anhydride (1 ml) was added dropwise to the cooled solution, and the resulting reaction solution was slowly heated up to $0°$ C. The reaction solution was washed with cold water and dried over anhydrous magnesium sulfate, after which the solvent was distilled off to leave the titled compound (830 mg; 75%) as pale brown oil.

NMR(CDCl$_3$), $\delta$ (ppm); 2.15–2.35 (2H, m), 3.70–4.00 (4H, m), 5.35–5.55 (1H, m).

(b) Diphenylmethyl 7-Phenylacetamido-3-(tetrahydrofuran-3-yl)thio-3-cephem-4-carboxylate A first solution was prepared by dissolving diphenylmethyl 7-phenylacetamido-3-acetylthio-3-cephem-4-carboxylate (280 mg) in hexamethylphosphoric triamide (2.8 ml), followed by ice-cooling the solution. A second solution was prepared by dissolving morpholine (0.87 ml) and triethylamine (1.39 ml) in benzene to give 10 ml of the second solution in benzene. The second solution (0.5 ml) was added dropwise to the first solution under ice-cooling and the resulting mixture was stirred under ice-cooling for 30 minutes. Then, the tetrahydrofuran-3-yl trifluoromethanesulfonate (830 g) prepared in step (a) above was added to the above mixture, and the resulting mixture was stirred for further 30 minutes. After adding cold water (5 ml) to the resulting reaction solution, the solution was extracted with ethyl acetate. The organic layer as obtained from the extraction was washed with an aqueous sodium chloride, dried over anhydrous magnesium sulfate and concentrated under reduced pressure to give a yellow oil. The oil was purified by silica gel column chromatography with elution using benzene-ethyl acetate (2:1, by volume) as eluent to collect fractions containing the titled compound, and the fractions thus collected were concentrated to afford the titled compound (210 mg; 71%) as pale yellow crystals.

Another procedure was also used to prepare the titled compound as detailed below.

A first solution was prepared by dissolving diphenylmethyl 7-phenylacetamido-3-acetylthio-3-cephem-4-carboxylate (3.4 g) in hexamethylphosphoric triamide (35 ml), followed by ice-cooling the solution. A second solution was prepared by dissolving morpholine (0.87 ml) and triethylamine (1.39 ml) in benzene to give 10 ml of the second solution. The second solution (6.0 ml) was added dropwise to the first solution under ice-cooling. The resulting mixture was stirred under the same temperature condition for 30 minutes, then added thereto 3-bromotetrahydrofuran (4.53 g) and further stirred at $40°$ C. for 2 hours. To the resulting reaction solution, ethyl acetate (50 ml) and cold water (50 ml) were added and then 1N aqueous citric acid was added to neutralize the solution to pH 5.0. Diisopropylether (25 ml) was added to the neutralized solution and the resulting solution was stirred well under ice-cooling to cause crystallization of the titled compound. Separation of the crystals by filtration, followed by drying the same gave the titled compound (1.8 g; 50%) as pale yellow crystals.

NMR(DMSO-d$_6$), $\delta$ (ppm); 1.50–2.30 (2H, m), 3.20–4.00 (7H, m), 3.55 (2H, s), 5.17 (1H, d, J=5 Hz), 5.66 (1H, dd, J=5 Hz, 9 Hz), 6.87 (1H, s), 7.10–7.50 (15H, m), 9.10 (1H, d, J=9 Hz).

(c) Diphenylmethyl 7-Amino-3-(tetrahydrofuran-3-yl)thio-3-cephem-4-carboxylate

Diphenylmethyl 7-phenylacetamido-3-(tetrahydrofuran-3-yl)thio-3-cephem-4-carboxylate (590 mg) was suspended in dichloromethane (8 ml) and the suspension was cooled to $-20°$ C. To the cooled suspension were added pyridine (0.24 ml) and phosphorus pentachloride, and the resulting mixture was stirred under ice-cooling for 2 hours and then cooled again to −20° C. Anhydrous methanol (0.81 ml) was then added rapidly and the mixture was stirred under ice-cooling for 3 hours. Cold water (10 ml) and dichloromethane(5 ml) were added to the resulting reaction solution, and the solution was stirred under ice-cooling for 30 minutes to deposit crystals. The mixture containing the crystals, after adding diisopropylether (10 ml) thereto, was stirred well and then filtered to obtain the crystals. The crystals were washed with cold water and with a small amount of dichloromethane, successively and then dried to afford the titled compound in the form of hydrochloride (270 mg; 53%) as pale yellow power.

NMR(DMSO-d6), δ (ppm); 1.60–2.30 (2H, m), 3.20–4.00 (7H, m), 5.08 (1H, d, J=5 Hz), 5.29 (1H, d, J=5 Hz), 6.84 (1H, s), 7.10–7.55 (10H, m).

(d) Diphenylmethyl 7-[(Z)-2-(2-tritylaminothiazol-4-yl)-2-methoxyiminoacetamido]-3-(tetrahydrofuran-3-yl)thio-3-cephem-4-carboxylate Vilthmyer reagent was prepared from dimethylformamide (52 mg) and trichloromethyl chloroformate (60 mg) in dichloromethane (1 ml) according to standard method. The Vilsmier reagent as prepared was cooled to −40° C., to which was then added a suspension of (Z)-2-(2-tritylaminothiazol-4-yl)-2-methoxyiminoacetic acid (266 mg) in dichloromethane (2 ml) and the resulting mixture was further stirred at −20° C. for 30 minutes to give a first solution. On the other hand, the diphenylmethyl 7-amino-3-(tetrahydrofuran-3-yl)thio-3-cephem-4-carboxylate hydrochloride (255 mg) was suspended in dichloromethane (2 ml), to which was added N,O-bistrimethylsilylacetamide (0.25 ml) to give a second, clear solution. The latter, second solution was added to the former, first solution, i.e. the solution containing the acetic acid derivative as activated with the Vilthmyer reagent as above, and the resulting mixture was stirred under ice-cooling for 60 minutes to effect the N-acylation reaction. The resulting reaction solution, after adding ice-cooled water thereto, was stirred well and then separated into organic and aqueous layers.

The organic layer so separated was washed with water and dried over magnesium sulfate, after which the solvent was distilled off under reduced pressure to leave an oily residue. The oil was purified by a silica gel-column chromatography (silica gel: 20 g) with elution using benzene-ethyl acetate (2:1 by volume) as eluent to collect fractions containing the titled compound, and the fractions collected were concentrated. The oily residue thus obtained was triturated with diisopropylether, followed by filtration and drying to afford the titled compound (340 mg; 84%).

NMR(CDCl3), δ (ppm); 1.60–2.30 (2H, m), 3.30–4.00 (7H, m), 4.03 (3H, s), 5.05 (1H, d, J=5 Hz), 5.80 (1H, dd, J=5 Hz, 9 Hz), 6.74 (1H, s), 6.91 (1H, S), 7.10–7.40 (26H, m).

(e) 7-[(Z)-2-(2-aminothiazol-4-yl)-2-methoxyiminoacetamido]-3-(tetrahydrofuran-3-yl)thio-3-cephem-4-carboxylic Acid Diphenylmethyl 7-[(Z)-2-(2-tritylaminothiazol-4-yl)-2-methoxyiminoacetamido]-3-(tetrahydrofuran-3-yl)thio-3-cephem-4-carboxylate (340 mg) was dissolved in anisole (1 ml), to which trifluoroacetic acid (2 ml) was then added under ice-cooling, and the resulting mixture was allowed to stand under ice-cooling for 90 minutes to effect the deprotection reactions. Then, the reaction solution was added dropwise to diisopropylether (15 ml) under ice-cooling to cause precipitation. The precipitate was taken up by filtration and suspended in cold water (3 ml) and the suspension was neutralized with an aqueous sodium hydrogen carbonate up to pH 7–8. The resulting solution was purified by a column chromatography on a column of a macroreticular resin "Diaion HP-20" (a product from Mitsubishi Kasei Co. Ltd., Japan) (20 ml) with elution using 30% aqueous methanol as eluent to collect fractions containing the titled compound. The fractions thus collected were concentrated to a small volume and lyophilized to afford the titled compound as sodium salt (140 mg; 65%)

NMR(D2O), δ (ppm); 1.60–2.45 (2H, m), 3.40–4.00 (7H, m), 3.96 (3H, s), 5.19 (1H, d, J=5 Hz), 5.73 (1H, d, J=5 Hz), 6.97 (1H, s).

EXAMPLE 2

Preparation of pivaloyloxymethyl 7-[(Z)-2-(2-aminothiazol-4-yl)-2-methoxyiminoacetamido]-3-(tetrahydrofuran-3-yl)thio-3-cephem-4-carboxylate Sodium 7-[(Z)-2-(2-aminothiazol-4-yl)-2-methoxyiminoacetamido]-3-(tetrahydrofuran-3-yl)thio-3-cephem-4-carboxylate (80 mg) (as obtained in Example 1) was dissolved in dimethylformamide (1.6 ml) and the solution was cooled to −20° C. The solution, after addition of iodomethyl pivalate (77 mg) thereto, was stirred at a temperature of −20° to −10° C. for 30 minutes (for the esterification reaciton), after which cold water (5 ml) was added to the reaction solution. The resulting mixture was extracted with ethyl acetate, and the organic layer separated was washed with an aqueous sodium chloride, dried over magnesium sulfate and concentrated under reduced pressure to leave a yellow oil. The oily residue was purified by a column chromatography on a silica gel column (15 g) with elution using ethyl acetate as eluent to collect fractions containing the titled compound. Concentration of the fractions so collected under reduced pressure gave the titled compound (65 mg; 68%) as white powder.

NMR(CDCl3), δ (ppm); 1.20 (9H, s), 1.85–2.00 (1H, m), 2.30–2.45 (1H, m) 3.50–4.10 (7H, m), 4.10 (3H, s), 5.13 (1H, d, J=5 Hz), 5.72 (1H, dd, J=5 Hz, 9 Hz), 5.80 (1H, d, J=7 Hz), 5.90 (1H, d, J=7 Hz), 7.15 (1H, s), 8.60 (½H, d, J=9 Hz), 8.65 (½H, d, J=9 Hz), 8.60–9.40 (2H, br-s).

EXAMPLE 3

Preparation of 7-[(Z)-2-(2-aminothiazol-4-yl)-2-hydroxyiminoacetamido]-3-(tetrahydrofuran-3-yl)thio-3-cephem-4-carboxylic acid (a) Diphenylmethyl 7-[(Z)-2-(2-tritylaminothiazol-4-yl)-2-trityloxyiminoacetamido]-3-(tetrahydrofuran-3-yl)thio-3-cephem-4-carboxylate Diphenylmethyl 7-amino-3-(tetrahydrofuran-3-yl)thio-3-cephem-4-carboxylate hydrochloride (270 mg) and sodium (Z)-2-(2-tritylaminothiazol-4-yl)-2-trityloxyiminoacetate (370 mg) were added to dichloromethane (5 ml) to give a translucent solution. The solution was cooled to −20° C., to which were then added, in order, pyridine (0.13 ml), phosphorus oxychloride (115 mg)

with 30 minutes later and cold water with 10 minutes later, thus to stop the reaction. The resulting reaction solution containing the above-titled compound as produced was stirred well and then separated into an organic layer and an aqueous layer.

The organic layer so separated was washed with water and dried over magnesium sulfate. The solvent was distilled off under reduced pressure to leave an oil. The oily residue was purified by a column chromatography on a column of silica gel (40 g) with elution using benzene-ethyl acetate (4:1 by volume) as eluent to collect fractions containing the titled compound. The fractions so collected were concentrated to a small volume to which diisopropylether was then added dropwise to deposit crystals. The crystals were separated by filtration, washed with diisopropylether and dried to afford the titled compound (320 mg; 53%)

NMR(CDCl$_3$), $\delta$ (ppm); 1.50–2.20 (2H, m), 3.20–4.00 (7H, m), 5.09 (1H, d, J=5 Hz), 5.90 (1H, dd, J=5 Hz, 9 Hz), 6.41 (1H, s), 6.69 (1H, s), 6.94 (1H, s), 7.00–7.40 (41H, m).

(b) 7-[(Z)-2-(2-Aminothiazol-4-yl)-2-hydroxyiminoacetamido]-3-(tetrahydrofuran-3-yl)thio-3-cephem-4-carboxylic Acid Diphenylmethyl 7- [(Z) -2-(2-tritylaminothiazol-4-yl) -2 -trityloxyiminoacetoamido ]-3 -(tetrahydrofuran-3-yl) thio-3-cephem-4-carboxylate (320 mg) was dissolved in anisole (1.5 ml). To the solution, trifluoroacetic acid (3 ml) was added under ice-cooling and 5 minutes later 2-mercaptobenzothiazole (96 mg) was added, and the resulting mixture was stirred under the same temperature condition for 90 minutes to effect the deprotection reacitons. The reaction solution was then added dropwise to ice-cooled diisopropylether, to cause precipitation. The precipitate thus formed was taken up by filtration, washed with diisopropylether and purified in the same manner as in Example 1(e), affording the titled compound as sodium salt (85 mg; 60%).

NMR (D$_2$O), $\delta$ (ppm); 1.60–2.45 (2H, m), 3.40–4.00 (7H, m), 5.25 (1H, d, J=5 Hz), 5.79 (1H, d, J=5 Hz), 6.95 (1H, s).

EXAMPLE 4

Preparation of pivaloyloxymethyl 7-[(Z)-2-(2-aminothiazol-4-yl)-2-hydroxyiminoacetamido]-3-(tetrahydrofuran-3-yl)thio-3-cephem-4-carboxylate Sodium 7- [(Z) -2-(2-aminothiazol-4-yl) -2-hydroxyiminoacetamido]-3 -(tetrahydrofuran-3 -yl) thio-3-cephem-4-carboxylate (55 mg) was dissolved in dimethylformamide (1 ml) and the solution was cooled to −20° C. Iodomethyl pivalate (41 mg) was added to the cooled solution and the resulting mixture was stirred under the same temperature condition as above for 30 minutes (for the esterification reaction). The resulting reaction solution, after addition of ethyl acetate and an aqueous sodium chloride thereto, was further stirred well and then separated into an organic layer and an aqueous layer. The organic layer so separated was washed with an aqueous sodium chloride and then dried over anhydrous magnesium sulfate. The solvent was distilled off under reduced pressure to leave an oil. The oily residue was purified by a column chromatography on a silica gel column (7 g) with elution using chloroform-methanol (10:1 by volume) as eluent to collect fractions containing the titled compound. The fractions so collected was concentrated under reduced pressure, affording the titled compound (35 mg; 53%).

NMR(CDCl$_3$), $\delta$ (ppm); 1.20 (9H, s), 1.60–2.50 (2H, m), 3.40–4.10 (7H, m), 5.03 (1H, d, J=5 Hz), 5.50 (2H, br-s), 5.70 (1H, dd, J=5 Hz, 9 Hz), 5.76 (1H, d, J=7 Hz), 5.87 (1H, d, J=7 Hz), 6.93 (1H, s), 9.80 (1H, br-s).

EXAMPLE 5

Preparation of 7-[(Z)-2-(2-aminothiazol-4-yl)-2-methoxyiminoacetamido]-3-tetrahydrofurfurylthio-3-cephem-4-carboxylic acid (a) Diphenylmethyl 7-phenylacetamido-3-tetrahydrofurfurylthio-3-cephem-4-carboxylate A first solution was prepared by dissolving diphenylmethyl 7-phenylacetamido-3-acetylthio-3-cephem-4-carboxylate (1.12 g) in hexamethylphosphoric triamide (12 ml), followed by ice-cooling. A second solution was prepared by dissolving morpholine (0.87 ml) and triethylamine (1.39 ml) in benzene to give 10 ml of the second solution. The second solution (2.0 ml) was added dropwise to the first solution under ice-cooling, and the resulting mixture was stirred at that temperature for 30 minutes, to which was then added tetrahydrofurfuryl bromide (1.65 g). The resultant mixture was further stirred at 40° C. for 2 hours. Ethyl acetate (50 ml) and cold water (50 ml) were added to the mixture, and the resulting mixture was stirred well and then separated into an organic layer and an aqueous layer. The organic layer was washed with an aqueous sodium chloride and dried over anhydrous magnesium sulfate and then the solvent was distilled off under reduced pressure to leave a yellow oil. The oily residue was purified by a column chromatography on a silica gel column (35 g) with elution using benzene-ethyl acetate (2:1 by volume) as eluent to collect fractions containing the titled compound. Concentration of the fractions collected gave the titled compound (850 mg; 70%) as pale yellow powder.

NMR spectroscopic analysis showed that this compound was a 1:1 mixture of the two diastereomers due to the asymmetric carbon atom on the 2-position of the tetrahydrofuran ring.

NMR (CDCl$_3$), $\delta$ (ppm); 1.30–2.10 (4H, m), 2.55–2.75 (2H, m), 3.20–4.00 (5H, m) 3.59 (2H, s), 4.88 ($\frac{1}{2}$H, d, J=5 Hz), 5.89 ($\frac{1}{2}$H, d, J=5 Hz), 5.60 ($\frac{1}{2}$H, dd, J=5 Hz, 9 Hz), 5.61 ($\frac{1}{2}$H, dd, J=5 Hz, 9 Hz), 6.69 (1H, d, J=9 Hz), 6.85 ($\frac{1}{2}$H, s), 6.86 ($\frac{1}{2}$H, s), 7.10–7.50 (15H, m).

(b) Diphenylmethyl 7-amino-3-tetrahydrofurfurylthio-3-cephem-4-carboxylate

Diphenylmethyl 7-phenylacetamido-3-tetrahydrofurfurylthio-3-cephem-4-carboxylate (850 mg) was N-deprotected and treated in the same manner as in Example 1(c) to afford the titled compound in the form of hydrochloride (540 mg, 73%) as pale yellow powder.

NMR(DMSO-d$_6$), $\delta$ (ppm); 1.30–2.00 (4H, m) 2.70–3.90 (7H, m), 5.05 (1H, d, J=5 Hz), 5.25 (1H, d, J=5 Hz), 6.85 (1H, s), 7.20–7.50 (10H, m).

(c) Diphenylmethyl 7-[(Z)-2-(2-tritylaminothiazol-4-yl)-2-methoxyiminoacetamido]-3-tetrahydrofurfuryl-3-cephem-4-carboxylate Diphenylmethyl 7-amino-3-tetrahydrofurfurylthio-3-cephem-4-carboxylate hydrochloride (260 mg) was condensed with (Z)-2-(2-tritylaminothiazol-4-yl)-2-methoxyiminoacetic acid (270 mg) in the same manner as in Example 1(d) to afford the titled compound (325 mg; 79%) as pale yellow powder.

NMR(CDCl$_3$), δ (ppm); 1.50–2.10 (4H, m), 2.82 (2H, d, J=7 Hz), 3.50–4.10 (5H, m), 4.03 (3H, s), 5.04 (1H, d, J=5 Hz), 5.77 (1H, dd, J=5 Hz, 9 Hz), 6.73 (1H, s), 6.91 (1H, s), 7.10–7.50 (27H, m).

(d) 7-[(Z)-2-(2-Aminothiazol-4-yl)-2-methoxyiminoacetamido]-3-3-tetrahydrofurfurylthio-3-cephem-4-carboxylic acid Diphenylmethyl 7-[(Z)-2-(2-tritylaminothiazol-4-yl)-2-methoxyiminoacetamido]-3-tetrahydrofurfurylthio-3-cephem-4-carboxylate (320 mg) was deprotected and then purified in the same manner as in Example 1(e) to afford the titled compound as sodium salt (103 mg; 51%).

NMR (D$_2$O), δ (ppm); 1.50–2.20 (4H, m), 2.88 (2H, d, J=7 Hz), 3.40–4.10 (5H, m), 3.94 (3H, s), 5.18 (1H, d, J=5 Hz), 5.73 (1H, d, J=5 Hz), 6.97 (1H, s).

EXAMPLE 6

Preparation of pivaloyloxymethyl 7-[(Z)-2-(2-aminothiazol-4-yl)-2-methoxyiminoacetamido]-3-tetrahydrofurfurylthio-3-cephem-4-carboxylate Sodium 7-[(Z)-2-(2-aminothiazol-4-yl)-2-methoxyiminoacetamido]-3-tetrahydrofurfurylthio-3-cephem-4-carboxylate (40 mg) was reacted with iodomethyl pivalate (38 mg), followed by purification, in the same manner as in Example 2 to give the titled compound (27 mg; 57%) as white powder.

NMR (CDCl$_3$), δ (ppm); 1.20 (9H, s), 1.50–2.20 (4H, m), 2.95 (2H, d, J=7 Hz), 3.50–4.20 (5H, m), 4.12 (3H, s), 5.06 (1H, d, J=5 Hz), 5.66 (1H, dd, J=5 Hz, 9 Hz), 5.76 (1H, d, J=7 Hz), 5.90 (1H, d, J=7 Hz), 7.13 (1H, s), 8,45 (1H, d, J=9 Hz), 9.00 (2H, br-s).

EXAMPLE 7

Preparation of 7-[(Z)-2-(2-aminothiazol-4-yl)-2-hydroxyiminoacetamido]-3-tetrahydrofurfurylthio-3-cephem-4-carboxylic acid

(a) Diphenylmethyl 7-[(Z)-2-(2-tritylaminothiazol-4-yl)-2-trityloxyiminoacetamide]-3-tetrahydrofurfurylthio-3-cephem-4-carboxylate Diphenylmethyl 7-amino-3-tetrahydrofurfurylthio-3-cephem- 4-carboxylate hydrochloride (530 mg) was reacted with sodium (Z)-2-(2-tritylaminothiazol-4-yl)-2-trityloxyiminoacetate (710 mg) in accordance with the reaction procedures used in Example 3(a). The crude product thus obtained was purified by a column chromatography on a silica gel column (40 g) with elution using benzene-ethyl acetate (4:1 by volume) as eluent to collect fractions containing the titled compound. After concentrating these fractions collected, the oily residue was triturated with diisopropylether, affording the titled compound (570 mg; 48%) as powder.

NMR (CDCl$_3$), δ (ppm); 1.45–2.10 (4H, m), 2.70–2.85 (2H, m), 3.30–3.95 (5H, m), 5.03 (1H, d, J=5 Hz), 5.85 (1H, dd, J=5 Hz, 9 Hz).

(b) 7-[(Z)-2-(2-Aminothiazol-4-yl)-2-hydroxyiminoacetamido]-3-tetrahydrofurfurylthio-3-cephem-4-carboxylic acid Diphenylmethyl 7-[(Z)-2-(2-tritylaminothiazol-4-yl)-2-trityloxyiminoacetamido]-3-tetrahydrofurfurylthio-3-cephem-4-carboxylate (300 mg) was treated and purified in accordance with the procedure of Example 3(b), affording the titled compound as sodium salt (72 mg; 53%).

NMR (D$_2$O), δ (ppm); 1.50–2.10 (4H, m), 2.88 (2H, d, J=7 Hz), 3.40–4.10 (5H, m), 5.19 (1H, d, J=5 Hz), 5.74 (1H, d, J=5 Hz), 6.93 (1H, s).

EXAMPLE 8

Preparation of pivaloyloxymethyl 7-[(Z)-2-(2-aminothiazol-4-yl)-2-hydroxyiminoacetamido]-3-tetrahydrofurfurylthio-3-cephem-4-carboxylate Sodium 7-[(Z)-2-(2-aminothiazol-4-yl)-2-hydroxyiminoacetamido]-3-tetrahydrofurfurylthio-3-cephem-4-carboxylate (50 mg) was reacted with iodomethyl pivalate (36 mg) and post-treated in the same manner as in Example 4, yielding the titled compound (15 mg; 25%) as colorless crystals.

NMR (DMSO-d$_6$ ), δ (ppm); 1.20 (9H, s), 1.50–2.10 (4H, m), 3.02 (2H, d, J=7 Hz), 3.60–4.00 (5H, m), 5.19 (1H, d, J=5 Hz), 5.73 (1H, dd, J=5 Hz, 9 Hz), 5.79 (1H, d, J=7 Hz), 5.86 (1H, d, J=7 Hz), 6.70 (1H, s), 9.50 (1H, d, J=9 Hz).

EXAMPLE 9

Preparation of 7-[(Z) -2-(2-aminothiazol-4-yl) -2-methoxyiminoacetamido]-3-(2,2-dimethyl-1,3-dioxolan-4-yl)methylthio-3-cephem-4-carboxylic acid

(a) Diphenylmethyl 7-[(Z)-2-(2-tritylaminothiazol-4-yl)-2-methoxyiminoacetamido]-3-acetylthio-3-cephem-4-carboxylate Diphenylmethyl 7-phenylacetamido-3-acetylthio-3-cephem-4-carboxylate (4.50 g) was dissolved in dichloromethane (60 ml) and the solution was cooled to −20° C. Pyridine (1.94 ml) and phosphorus pentachloride (2.50 g) were added to the cooled solution and the resulting mixture was stirred under ice-cooling for 2 hours and then cooled again to −20° C. Anhydrous methanol (6.47 ml) was rapidly added to the reaction solution while the temperature being kept below 0° C., and the resulting mixture was stirred under ice-cooling for 3 hours. To the resulting reaction solution, after having been cooled to −20° C., were added cold water (60 ml) and dichloromethane (60 ml) and the mixture was further stirred under ice-cooling for 30 minutes. Then, the reaction solution was neutralized with an aqueous sodium hydrogen carbonate up to pH 8.0, stirred well and separated into layers.

The organic layer so separated was washed with an aqueous sodium choride, dried over magnesium sulfate and concentrated to a volume of about 60 ml. To the concentrate was added (Z)-2-(2-tritylaminothiazol-4-yl)-2-methoxyiminoacetic acid (3.55 g) and the mixture was cooled to −20° C. Pyridine (1.94 ml) was added to the cooled mixture under stirring and after the lapse of 10 minutes phosphorus oxychloride (1.72 g) was added dropwise thereto under the same temperature condition. Continuing the stirring for further 10 minutes, the reaction was stopped by the addition of cold water, and two layers were separated.

The organic layer was washed with water and dried over magnesium sulfate. The solvent was then distilled off to leave an oily residue which was purified by a column chromatography on a silica gel column (150 g) with elution using benzene-ethyl acetate (7:1 by volume) as eluent. Fractions containing the titled compound were collected and concentrated and the oily residue was triturated with diisopropylether, followed by filtration and drying, affording the titled compound (5.4 g; 77%).

NMR (CDCl$_3$), δ (ppm); 2.10 (3H, s), 3.33 (1H, d, J=18 Hz), 3.82 (1H, d, J=18 Hz), 4.10 (3H, s), 5.11 (1H, d, J=5 Hz), 5.92 (1H, dd, J=5 Hz, 9 Hz), 6.79 (1H, s), 6.95 (1H, s), 7.10–7.50 (27H, m).

(b) Diphenylmethyl 7-[(Z)-2-(2-tritylaminothiazol-4-yl)-2-methoxyiminoacetamido]-3-(2,2-dimethyl-1,3-dioxolan-4-yl)methylthio-3-cephem-4-carboxylate A first solution was prepared by dissolving diphenylmethyl 7-[(Z)-2-(2-tritylaminothiazol-4-yl)-2-methoxyiminoacetamido]-3-acetylthio-3-cephem-4-carboxylate (433 mg) in hexamethylphosphoric triamide (5 ml), followed by ice-cooling. A second solution was prepared by dissolving morpholine (0.87 ml) and triethylamine (1.39 ml) in benzene to give a 10 ml solution. The second solution (0.5 ml) was added dropwise to the first solution under stirring and the stirring was continued under the same temperature condition as above for further 30 minutes. To the resulting reaction solution was added an amount (200 mg) of a trifluoromethanesulfonic acid ester (that is, 2,2-dimethyl-1,3-dioxolan-4-ylmethyl trifluoromethanesulfonate) which was prepared from 2,2-dimethyl-1,3-dioxolan-4-yl-methanol (660 mg), pyridine (0.49 ml) and trifluoromethanesulfonic acid anhydride (1.69 g) in accordance with the procedure of Example 1(a). The resulting reaction solution was stirred under ice-cooling for 60 minutes, after which cold water was added thereto and the mixture was extracted with ethyl acetate.

The organic layer, i.e. the extract, was washed with water and dried over magnesium sulfate and then the solvent was distilled off to leave an oily residue. The residual oil was purified by a column chromatography on a silica gel column (35 g) with elution using benzene-ethyl acetate (2:1 by volume) as eluent. Fractions containing the titled compound were collected from the elution and concentrated and the resulting oily residue was triturated with hexane-diisopropylether (1:1 by volume), followed by filtration and drying, to afford the titled compound (340 mg; 72%).

NMR (CDCl$_3$), δ (ppm); 1.30 (3H, s), 1.37 (3H, s), 2.70–2.95 (2H, m), 3.40–4.10 (5H, m), 4.04 (3H, s), 5.05 (1H, d, J=5 Hz), 5.82 (1H, dd, J=5 Hz, 9 Hz), 6.75 (1H, s), 6.92 (1H, s), 6.93 (1H, s), 7.20–7.40 (26H, m).

(c) 7-[(Z)-2-(2-aminothiazol-4-yl)-2-methoxyiminoacetamido]-3-(2,2-dimethyl-1,3-dioxolan-4-yl)methylthio-3-cephem-4-carboxylic acid Diphenylmethyl 7-[(Z)-2-(2-tritylaminothiazol-4-yl)-2-methoxyiminoacetamido]-3-(2,2-dimethyl-1,3-dioxolan-4-yl)methylthio-3-cephem-4-carboxylate (320 mg) was dissolved in anisole (0.6 ml), to which was then added trifluoroacetic acid (1.6 ml) under ice-cooling and stirring. The resulting reaction solution was further stirred under the same temperature condition for 60 minutes and then added dropwise to diisopropylether (15 ml) while being under ice-cooling condition, when precipitation occurred. The precipitate was taken up by filtration and suspended in cold water and neutralized with an aqueous sodium hydrogen carbonate to pH 7–8.

The resulting solution was purified by a column chromatography on a column of Diaion HP-20 (50 ml) with successive elutions with water, 10% aqueous methanol, 20% aqueous methanol and 30% aqueous methanol as eluents. Fractions containing the titled compound from the elutions were collected, concentrated and lyophilized to give the titled compound as sodium salt (83 mg; 44%).

NMR(D$_2$O), δ (ppm); 1.32 (3H, s), 1.40 (3H, s), 2.93 (2H, d, J=7 Hz), 3.40–4.30 (5H, m), 3.94 (3H, s), 5.19 (1H, d, J=5 Hz), 5.72 (1H, d, J=5 Hz), 6.96 (1H, s).

EXAMPLE 10

Preparation of pivaloyloxymethyl 7-[(Z)-2-(2-aminothiazol-4-yl)-2-methoxyiminoacetamido]-3-(2,2-dimethyl-1,3-dioxolan-4-yl)methylthio-3-cephem-4-carboxylate Sodium 7-[(Z)-2-(2-aminothiazol-4-yl)-2-methoxyiminoacetamido]-3-(2,2-dimethyl-1,3-dioxolan-4-yl)methylthio-3-cephem-4-carboxylate (58 mg) was reacted with iodomethyl pivalate (51 mg), followed by purifying the reaction product in the same manner as in Example 2, yielding the titled compound (45 mg; 66%) as pale yellow powder.

NMR(CDCl$_3$), δ (ppm); 1.30 (3H, s), 1.38 (3H, s), 2.80–3.00 (2H, m), 3.50–4.30 (5H, m), 4.02 (3H, s), 5.06 (1H, d, J=5 Hz), 5.25 (2H, br-s), 5.70–5.95 (3H, m), 6.83 (1H, s), 7.42 (1H, d, J=9 Hz).

EXAMPLE 11

Preparation of 7-[(Z)-2-(2-aminothiazol-4-yl)-2-methoxyiminoacetamido]-3-(tetrahydropyran-4-yl)thio-3-cephem-4-carboxylic acid (a) Diphenylmethyl 7-phenylacetamido-3-(tetrahydropyran-4-yl)thio-3-cephem-4-carboxylate A first solution was prepared by dissolving diphenylmethyl 7-phenylacetamido-3-(tetrahydropyran-4-yl)thio-3-cephem-4-carboxylate (2.24 g) in hexamethylphosphoric triamide (20 ml), followed by ice-cooling. A second solution was prepared by dissolving morpholine (0.87 ml) and triethylamine (1.39 ml) in benzene to give a 10 ml solution. The second solution (94.0 ml) was added dropwise to the first solution under stirring and the stirring was continued under the same temperature condition for further 30 minutes. To the resulting reaction solution was added an ester of trifluoromethanesulfonic acid which was prepared from 4-hydroxytetrahydropyran (3.0 g), pyridine (2.86 ml) and trifluoromethanesulfonic acid anhydride (5.93 ml) in accordance with the procedure of Example 1(a). The resulting mixture was stirred at 5° C. for further 60 minutes, to which were then added ice-cooled water (60 ml) and ethyl acetate (60 ml), and the resulting mixture was neutralized with 1N aqueous citric acid solution to pH 5.0. After the addition of diisopropylether (30 ml) to the neutralized solution under ice-cooling and stirring followed by the continued stirring, crystals formed were taken up by filtration, washed with ice-cooled water and with diisopropylether, in order, and dried to afford the titled compound (1.49 g; 61%) as pale yellow crystals.

NMR (CDCl$_3$), δ (ppm); 1.30–1.80 (4H, m), 2.80–3.90 (7H, m), 3.60 (2H, s), 4.93 (1H, d, J=5 Hz), 5.62 (1H, dd, J=5 Hz, 9 Hz), 6.32 (1H, d, J=9 Hz), 6.90 (1H, s), 7.10–7.40 (15H, m).

(b) Diphenylmethyl 7-amino-3-(tetrahydropyran-4-yl)-thio-3-cephem-4-carboxylate

Diphenylmethyl 7-phenylacetamido-3-(tetrahydropyran-4-yl)thio-3-cephem-4-carboxylate (1.28 g) was dissolved in dichloromethane (15 ml) and the solution was cooled to −20° C. To the solution, pyridine (0.52 ml) and phosphorus pentachloride (665 mg) were added and the resulting mixture was stirred under ice-cooling for 2 hours and then further cooled to −30° C. Anhydrous methanol (1.72 ml) was rapidly added to the cooled reaction solution while maintaining the temperature below 0° C. and the mixture was stirred under ice-cooling for 3 hours and then further cooled again to −20° C. After adding a 15% aqueous sodium chloride solution to the reaction solution, the pH thereof was adjusted to 1 with the addition of aqueous sodium hydrogen carbonate and the reaction solution was further stirred for 30 minutes. Upon subsequent addition of diisopropylether (30 ml), precipitate was deposited from the solution, taken up by filtration, washed with cold water and with diisopropylether successively and then dried to yield the titled compound in the form of hydrochloride (970 mg; 87%).

NMR(DMSO-d$_6$), δ (ppm); 1.20–2.00 (4H, m), 3.00–4.00 (7H, m), 5.01 (1H, d, J=5 Hz), 5.25 (1H, d, J=5 Hz), 6.84 (1H, s), 7.10–7.50 (10H, m).

(c) Diphenylmethyl 7-[(Z)-2-(2-tritylaminothiazol-4-yl)-2-methoxyiminoacetamido]-3-(tetrahydropyran-4-yl)thio-3-cephem-4-carboxylate Diphenylmethyl 7-amino-3-(tetrahydropyran-4-yl) thio-3-cephem-4-carboxylate hydrochloride (290 mg) was reacted with (Z)-2-(2-tritylaminothiazol-4-yl)-2-methoxyiminoacetic acid (267 mg), followed by purifying the reaction product in accordance with the procedure of Example (d), to afford the titled compound (360 mg; 79%).

NMR (CDCl$_3$), δ (ppm); 1.40–1.80 (4H, m), 2.90–3.90 (7H, m), 4.03 (3H, s), 5.05 (1H, d, J=5 Hz), 5.80 (1H, dd, J=5 Hz, 9 Hz), 6.73 (1H, s), 6.82 (1H, d, J=9 Hz), 6.96 (1H, s), 7.10–7.40 (26H, m).

(d) 7-[(Z)-2-(2-Aminothiazol-4-yl)-2-methoxyiminoacetamido]-3-(tetrahydropyran-4-yl)thio-3-cephem-4-carboxylic acid Diphenylmethyl 7-[(Z)-2-(2-tritylaminothiazol-4-yl)-2-methoxyiminoacetamido]-3-(tetrahydropyran-4-yl)thio-3-cephem-4-carboxylate (340 mg) was deprotected, followed by purifying the reaction product in accordance with the procedure of Example 1(e), to afford the titled compound as sodium salt (170 mg; 86%).

NMR(D$_2$O), δ (ppm); 1.40–2.10 (4H, m), 3.15 –4.00 (7H, m), 3.95 (3H, s), 5.22 (1H, d, J=5 Hz), 5.75 (1H, d, J=5 Hz), 6.97 (1H, s).

EXAMPLE 12

Preparation of pivaloyloxymethyl 7-[(Z)-2-(2-aminothiazol-4-yl)-2-methoxyiminoacetamido]-3-(tetrahydropyran-4-yl)thio-3-cephem-4-carboxylate Sodium 7-[(Z)-2-(2-aminothiazol-4-yl)-2-methoxyiminoacetamido]-3-(tetrahydropyran-4-yl)thio-3-cephem-4-carboxylate (90 mg) was reacted with iodomethyl pivalate (84 mg), followed by purifying the reaction product in accordance with the procedure of Example 2, affording the titled compound (82 mg; 77%).

NMR (CDCl$_3$), δ (ppm); 1.20 (9H, s), 1.50–2.00 (4 h, m), 3.10–4.10 (7H, m), 4.03 (3H, s), 5.08 (1H, d, J=5 Hz), 5.20–6.20 (2H, br-s), 5.80–6.00 (3H, m), 6.88 (1H, s), 7.54 (1H, d, J=9 Hz).

EXAMPLE 13

Preparation of 7-[(Z)-2-(2-aminothiazol-4-yl)-2-hydroxyiminoacetamido]-3-(tetrahydropyran-4-yl)thio-3-cephem-4-carboxylic acid (a) Diphenylmethyl 7-[(Z)-2-(2-tritylaminothiazol-4-yl)-2-trityloxyiminoacetamido]-3-(tetrahydropyran-4-yl)thio-3-cephem-4-carboxylate Diphenylmethyl 7-amino-3-(tetrahydropyran-4-yl)thio-3-cephem-4-carboxylate hydrochloride (290 mg) was reacted with (Z)-2-(2-tritylaminothiazol-4-yl)-2-trityloxyiminoacetic acid (403 mg), followed by purifying the reaction product in accordance with the procedure of Example 1(d), affording the titled compound (500 mg; 88%).

NMR(CDCl$_3$), δ (ppm); 1.40–1.80 (4H, m), 2.90–3.90 (7H, m), 5.04 (1H, d, J=5 Hz), 5.88 (1H, dd, J=5 Hz, 9 Hz), 6.39 (1H, s), 6.67 (1H, s), 6.95 (1H, s), 7.10–7.40 (41H, m).

(b) 7-[(Z)-2-(2-Aminothiazol-4-yl)-2-hydroxyiminoacetamido]-3-(tetrahydropyran-4-yl)thio-3-cephem-4-carboxylic Acid Diphenylmethyl 7-[(Z)-2-(2-tritylaminothiazol-4-yl) -2-trityloxyiminoacetamido]-3-(tetrahydropyran-4-yl)thio-3-cephem-4-carboxylate (460 mg) was treated and purified in accordance with the procedure of Example 3(b), affording the titled compound as sodium salt (130 mg; 63%).

NMR(D$_2$O), δ (ppm); 1.30–2.00 (4H, m), 3.10–4.00 (7H, m), 5.20 (1H, d, J=5 Hz), 5.75 (1H, d, J=5 Hz), 6.92 (1H, s).

EXAMPLE 14

Preparation of pivaloyloxymethyl 7-[(Z)-2-(2-aminothiazol-4-yl)-2-hydroxyiminoacetamido]-3-(tetrahydropyran-4-yl)thio-3-cephem-4-carboxylate Sodium 7-[(Z)-2-(2-aminothiazol-4-yl)-2-hydroxyiminoacetamido]-3-(tetrahydropyran-4-yl)thio-3-cephem-4-carboxylate (85 mg) was reacted with iodomethyl pivalate (61 mg), followed by purifying the reaction product in accordance with the procedure of Example 4, yielding the titled compound (56 mg, 55%).

NMR(CDCl$_3$), δ (ppm); 1.20 (9H, s), 1.50–2.00 (4H, m), 3.10–3.70 (5H, m), 3.70–4.15 (2H, m), 5.06 (1H, d, J=5 Hz), 4.60–6.00 (2H, br-s), 5.73 (1H, dd, J=5 Hz, 9 Hz), 5.80 (1H, d, J=6 Hz), 5.90 (1H, d, J=6 Hz), 6.97 (1H, s), 9.95 (1H, d, J=9 Hz).

EXAMPLE 15

Preparation of 7-[(Z)-2-(2-aminothiazol-4-yl)-2-methoxyiminoacetamido]-3-(2,2-dimethyl-1,3-dioxan-4-yl)methylthio-3-cephem-4-carboxylic acid (a) Diphenylmethyl 7-[(Z)-2-(2-tritylaminothiazol-4-yl)-2-methoxyiminoacetamido]-3-(2,2-dimethyl-1,3-dioxan-4-yl)methylthio-3-cephem-4-carboxylate A first solution was prepared by dissolving diphenylmethyl 7-[(Z)-2-(2-tritylaminothiazol-4-yl)-2-methoxyiminoacetamido]-3-acetylthio-3-cephem-4-carboxylate (520 mg) in hexamethylphosphoric triamide (6 ml), followed by ice-cooling the solution. A second solution was prepared by dissolving morpholine (0.87 ml) and triethylamine (1.39 ml) in benzene to give a 10 ml solution. The second solution (0.6 ml) was added dropwise to the first solution under ice-cooling and stirring and the resulting solution was stirred under the same temperature condition as above for further 30 minutes. To the reaction solution was added 2,2-dimethyl-1,3-dioxan-4-ylmethyl trifluoromethanesulfonate (250 mg) and the mixture was stirred under ice-cooling for 60 minutes. The resulting reaction solution, after adding cold water thereto, was extracted with ethyl acetate.

The organic layer separated from the extraction was washed with water and dried over magnesium sulfate, after which the solvent was distilled off to leave an oil. The oily residue was purified by a column chromatography on a silica gel column (35 mg) with elution using benzene-ethyl acetate (2:1 by volume) as eluent to collect fractions containing the titled compound. The fractions collected were concentrated and the resulting oily residue was triturated with hexane-diisopropylether (1:1 by volume) and the powdery mass thus formed was taken up by filtration and dried to afford the titled compound (330 mg; 57%).

NMR(CDCl$_3$), δ (ppm); 1.30 (3H, s), 1.39 (3H, s), 1.50–1.80 (2H, m), 2.60–2.90 (2H, m), 3.30–4.10 (5H, m), 4.03 (3H, s), 5.04 (1H, d, J=5 Hz), 5.77 (1H, dd, J=5 Hz, 9 Hz), 6.73 (1H, s), 6.90 (1H, s), 7.10–7.50 (27H, m).

(b) 7-[(Z)-2-(2-Aminothiazol-4-yl)-2-methoxyiminoacetamido]-3-(2,2-dimethyl-1,3-dioxan-4-yl)methylthio-3-cephem-4-carboxylic acid Diphenylmethyl 7-[(Z)-2-(2-tritylaminothiazol-4-yl)-2-methoxyiminoacetamido]-3-(2,2-dimethyl-1,3-dioxan-4-yl)methylthio-3-cephem-4-carboxylate (310 mg) was treated and purified in accordance with the procedure of Example 9 (c), yielding the titled compound as sodium salt (100 mg; 54%).

NMR(D$_2$O), δ (ppm); 1.34 (3H, s), 1.40 (3H, s), 1.65–1.95 (2H, m), 2.60–2.90 (2H, m), 3.35–4.40 (5H, m), 3.94 (3H, s), 5.18 (1H, d, J=5 Hz), 5.71 (1H, d, J=5 Hz), 6.97 (1H, s).

EXAMPLE 16

Preparation of pivaloyloxymethyl 7-[(Z)-2-)2-aminothiazol-4-yl)-2-methoxyiminoacetamido]-3-(2,2-dimethyl-1,3-dioxan-4-yl)methylthio-3-cephem-4-carboxylate Sodium 7-[(Z)-2-(2-aminothiazol-4-yl)-2-methoxyiminoacetamido]-3-(2,2-dimethyl-1,3-dioxan-4-yl)methylthio-3-cephem-4-carboxylate (70 mg) was reacted with iodomethyl pivalate (60 mg), followed by purifying the reaction product in accordance with the procedure of Example 2, affording the titled compound (55 mg; 67%).

NMR(CDCl$_3$), δ (ppm); 1.21 (9H, s), 1.32 (3H, s), 1.39 (3H, s), 1.65–1.95 (2H, m), 2.70–3.00 (2H, m), 3.40–3.65 (3H, m), 3.90–4.30 (2H, m), 4.04 (3H, s), 5.08 (1H, d, J=5 Hz), 5.70–5.90 (1H, m), 5.80 (1H, d, J=7 Hz), 5.88 (1H, d, J=7 Hz), 6.92 (1H, s), 7.60 (1H, d, J=9 Hz).

EXAMPLE 17

Preparation of 7-[(Z)-2-(2-aminothiazol-4-yl)-2-hydroxyiminoacetamido]-3-(2,2-dimethyl-1,3-dioxan-4-yl)methylthio-3-cephem-4-carboxylic acid (a) Diphenylmethyl 7-[(Z)-2-(2-tritylaminothiazol-4-yl)-2-trityloxyiminoacetamido]-3-acetylthio-3-cephem-4-carboxylate The procedure of Example 9(a) was repeated except that (Z)-2-(2-tritylaminothiazol-4-yl)-2-trityloxyiminoacetic acid (5.38 g) was used in place of (Z)-2-(2-tritylaminothiazol-4-yl)-2-methoxyiminoacetic acid (3.55 g), giving the titled compound (5.30 g) as yellow powder.

NMR(CDCl$_3$), δ (ppm); 2.10 (3H, s), 3.18 (1H, d, J=18 Hz), 3.72 (1H, d, J=18 Hz), 5.12 (1H, d, J=5 Hz), 6.06 (1H, dd, J=5 Hz, 9 Hz), 6.39 (1H, s), 6.72 (1H, s), 6.96 (1H, s), 7.10–7.50 (41H, m).

(b) Diphenylmethyl 7-[(Z)-2-(2-tritylaminothiazol-4-yl)-2-trityloxyiminoacetamido]-3-(2,2-dimethyl-1,3-dioxan-4-yl)methylthio-3-cephem-4-carboxylate Diphenylmethyl 7-[(Z)-2-(2-tritylaminothiazol-4-yl)-2-trityloxyiminoacetamido]-3-acetylthio-3-cephem-4-carboxylate (656 mg) was subjected to the reaction according to the procedure of Example 15(a) to give a crude product of the titled compound. The crude product was purified by a column chromatography on a silica gel column (40 g) with elution using benzene-ethyl acetate (7:1 by volume) as eluent to collect fractions containing the titled compound. The fractions collected were concentrated and the oily concentrate was triturated with diisopropylether-hexane (2:1 by volume), giving the titled compound (420 mg; 59%) as powder.

NMR (CDCl$_3$ ), δ (ppm); 1.30 (3H, s), 1.37 (3H, s), 1.50–1.80 (2H, m), 2.60–2.90 (2H, m), 3.20–3.70 (3H, m), 3.80–4.20 (2H, m), 5.01 (1H, d, J=5 Hz), 5.88 (1H, dd, J=5 Hz, 9 Hz), 6.42 (1H, s), 6.70 (1H, s), 6.91 (1H, s), 7.00–7.50 (41H, m).

(c)

7-[(Z)-2-(2-Aminothiazol-4-yl)-2-hydroxyiminoacetamido]-3-(2,2-dimethyl-1,3-dioxan-4-yl)methylthio-3-cephem-4-carboxylic acid Diphenylmethyl 7-[(Z)-2-(2-tritylaminothiazol-4-yl)-2-trityloxyiminoacetamido]-3-(2,2-dimethyl-1,3-dioxan-4-yl)methylthio-3-cephem-4-carboxylate (420 mg) was subjected to deprotection reaction according to the procedure of Example 3 (b). The crude product thus obtained was purified by a column chromatography on a column of Diaion HP-20 (50 ml) with elutions using water, 15% aqueous methanol and 30% aqueous methanol, in order, as eluents. Fractions containing the titled compound were collected, concentrated and finally lyophilized to afford the titled compound (60 mg; 30%).

NMR($D_2O$), δ (ppm); 1.33 (3H, s), 1.40 (3H, s), 1.65–1.95 (2H, m), 2.65–2.90 (2H, m), 3.47 (1H, d, J=16 Hz), 3.50–3.80 (1H, m), 3.78 (1H, d, J=16 Hz), 4.00–4.30 (2H, m), 5.20 (1H, d, J=5 Hz), 5.74 (1H, d, J=5 Hz), 6.93 (1H, s).

EXAMPLE 18

Preparation of pivaloyloxymethyl 7-[(Z)-2-(2-aminothiazol-4-yl)-2-hydroxyiminoacetamido]-3-(2,2-dimethyl-1,3-dioxan-4-yl)methylthio-3-cephem-4-carboxylate Sodium 7-[(Z)-2-(2-aminothiazol-4-yl)-2-hydroxyiminoacetamido]-3-(2,2-dimethyl-1,3-dioxan-4-yl)methylthio-3-cephem-4-carboxylate (60 mg) was reacted with iodomethyl pivalate (40 mg), followed by purifying the reaction product in accordance with the procedure of Example 4, yielding the titled compound (42 mg; 60%).

NMR ($CDCl_3$), δ (ppm); 1.20 (9H, s), 1.30 (3H, s), 1.36 (3H, s), 1.60–2.00 (2H, m), 2.70–3.10 (2H, m), 3.40–3.80 (3H, m), 3.90–4.30 (2H, m), 5.06 (1H, d, J=5 Hz), 5.20–6.20(2H, br-s), 5.60–5.80 (1H, m), 5.79 (1H, d, J=7 Hz), 5.88 (1H, d, J=7 Hz), 7.04 (1H, s), 9.35 (1H, d, J=9 Hz).

EXAMPLE 19

Preparation of 7-[(Z)-2-(2-aminothiazol-4-yl)-2-methoxyimionacetamido]-3-(1,3-dioxan-5-yl)thio-3-cephem-4-carboxylic acid (a) Diphenylmethyl 7-[(Z)-2-(2-tritylaminothizol-4-yl)-2-methoxyiminoacetamido]-3-(1,3-dioxan-5-yl)thio-3-cephem-4-carboxylate The procedure of Example 9(b) for the intended reaction was repeated except that 1,3-dioxan-5-yl trifluoromethanesulfonate (236 mg) was used in place of 2,2-dimethyl-1,3-dioxolan-4-ylmethyl trifluoromethanesulfonate.

The crude reaction product thus formed was purified by a column chromatography on a silica gel column (70 g) with elution using benzene-ethyl acetate (3:1 by volume) as eluent to collect fractions containing the titled compound. The fractions collected were concentrated and the oily concentrated was triturated with diisopropyletherhexane (2:1 by volume), affording the titled compound (180 mg; 39%) as powder.

NMR($CDCl_3$), δ (ppm); 3.10–4.00 (7H, m), 4.02 (3H, s), 4.46 (1H, d, J=7 Hz), 4.86 (1H, d, J=7 Hz), 5.04 (1H, d, J=5 Hz), 5.82 (1H, dd, J=5 Hz, 9 Hz), 6.70 (1H, s), 6.91 (1H, s), 6.93 (1H, s), 7.20–7.40 (26H, m).

(b)

7-[(Z)-2-(2-Aminothiazol-4-yl)-2-methoxyiminoacetamido]-3-(1,3-dioxan-5-yl)thio-3-cephem-4-carboxylic Acid Diphenylmethyl 7-[(Z)-2-(2-tritylaminothiazol-4-yl)-2-methoxyiminoacetamido]-3-(1,3-dioxan-5-yl)thio-3-cephem-4-carboxylate (180 mg) was subjected to deprotection reaction, followed by purifying the reaction product according to the procedure of Example 1(e), giving the titled compound as sodium salt (74 mg; 71%).

NMR($D_2O$), δ (ppm); 3.20–4.30 (7H, m), 4.02 (3H, s), 4.80 (1H, d, J=8 Hz), 4.90 (1H, d, J=8 Hz), 5.19 (1H, d, J=5 Hz), 5.73 (1H, d, J=5 Hz), 6.94 (1H, s).

EXAMPLE 20

Preparation of pivaloyloxymethyl 7-[(Z)-2-(2-aminothiazol-4-yl)-2-methoxyiminoacetamido]-3-(1,3-dioxan-5-yl)thio-3-cephem-4-carboxylate Sodium 7-[(Z) -2-(2-aminothiazol-4-yl) -2-methoxyiminoacetamido]-3-(1,3-dioxan-5-yl) thio-3-cephem-4-carboxylate (45 mg) was reacted with iodomethyl pivalate (42 mg), followed by purifying the reaction product in accordance with the procedure of Example 2, giving the titled compound (30 mg; 56%).

NMR($CDCl_3$), δ (ppm); 1.21 (9H, s), 3.20–3.80 (5H, m), 3.90–4.30 (2H, m), 4.04 (3H, s), 4.60 (1H, d, J=7 Hz), 4.91 (1H, d, J=7 Hz), 5.06 (1H, d, J=5 Hz), 5.13 (2H, br-s), 5.84 (2H, s), 5.90 (1H, dd, J=5 Hz, 9 Hz), 6.88 (1H, s), 7.18 (1H, d, J=9 Hz).

EXAMPLE 21

Preparation of 7-[(Z)-2-(2-aminothiazol-4-yl)-2-hydroxyiminoacetamido]-3-(1,3-dioxan-5-yl)thio-3-cephem-4-carboxylic acid (a) Diphenylmethyl 7-[(Z)-2-(2-tritylaminothiazol-4-yl)-2-trityloxyiminoacetamido]-3-(1,3-dioxan-5-yl)thio-3-cephem-4-carboxylate Diphenylmethyl 7-[(Z)-2-(2-tritylaminothiazol-4-yl)-2-trityloxyiminoacetamido]-3-acetylthio-3-cephem-4-carboxylate (550 mg) was reacted as in Example 19(a). The crude reaction product was purified by a column chromatography on a silica gel column (70 g) with elution using benzene-ethyl acetate (10:1 by volume) as eluent to collect fractions containing the titled compound. The fractions collected were concentrated and then triturated with diisopropylether-hexan (3:1 by bolume), yielding the titled compound (300 mg; 52%) as powder.

NMR($CDCl_3$), δ (ppm); 3.10–4.10 (7H, m), 4.47 (1H, d, J=7 Hz), 4.87 (1H, d, J=7 Hz), 5.04 (1H, d, J=5 Hz), 5.94 (1H, dd, J=5 Hz, 9 Hz), 6.39 (1H, s), 6.65 (1H, s), 6.96 (1H, s), 7.10–7.50 (41H, m).

(b)

7-[(Z)-2-(2-Aminothiazol-4-yl)-2-hydroxyiminoacetamido]-3-(1,3-dioxan-5-yl)thio-3-cephem-4-carboxylic Acid Diphenylmethyl 7-[(Z)-2-(2-tritylaminothiazol-4-yl)-2-trityloxyiminoacetamido]-3-(1,3-dioxan-5-yl)thio-3-cephem-4-carboxylate (300 mg) was used for the reaction, followed by purifying the reaction product in accordance with the general procedure of Example 3(b), giving the titled compound as sodium salt (80 mg; 59%).

NMR (D$_2$O), δ (ppm); 3.20–4.30 (7H, m), 4.83 (1H, d, J=9 Hz), 4.92 (1H, d, J=9 Hz), 5.22 (1H, d, J=5 Hz), 5.79 (1H, d, J=5 Hz), 6.93 (1H, s).

EXAMPLE 22

Preparation of pivaloyloxymethyl 7-[(Z)-2-(2-aminothiazol-4-yl)-2-hydroxyiminoacetamido]-3-(1,3-dioxan--yl)thio-3-cephem-4-carboxylate Sodium 7-[(Z)-2-(2-aminothiazol-4-yl) -2-hydroxyiminoacetamido]-3-(1,3-dioxan-5-yl)thio-3-cephem-4-carboxylate (50 mg) was reacted with iodomethyl pivalate, followed by purifying the reaction product in accordance with the procedure of Example 4, giving the titled compound (30 mg; 50%).

NMR (CDCl$_3$) δ (ppm); 1.20 (9H, s), 3.20–3.80 (5H, m), 3.90–4.30 (2H, m), 4.62 (1H, d, J=7 Hz), 4.91 (1H, d, J=7 Hz), 5.09 (1H, d, J=5 Hz), 5.70–6.00 (5H, m), 6.92 (1H, s).

EXAMPLE 23

Preparation of 7-[(Z)-2-(2-aminothiazol-4-yl)-2-methoxyiminoacetamido]-3-(tetrahydropyran-2-yl)methylthio-3-cephem-4-carboxylic acid (a) Diphenylmethyl 7-phenylacetamido-3-(tetrahydropyran-2-yl)methylthio-3-cephem-4-carboxylate Diphenylmethyl 7-phenylacetamido-3-acetylthio-3-cephem-4-carboxylate (1.68 g) was reacted with 2-bromomethyltetrahydropyran (1.92 ml) in accordance with the procedure of Example 1(b). The crude reaction product was purified by a column chromatography on a silica gel column (40 g) with elution using benzene-ethyl acetate (4:1 by volume) as eluent to collect fractions containing the titled compound. The fractions collected were concentrated and the oily residue was triturated with diisopropylether to give the titled compound (1.42 g; 71%) as powder.

NMR spectroscopic analysis showed that this compound was a 1:1 mixture of the two diastereomers due to the asymmetric carbon atom on the 2-position of the tetrahydropyran ring.

NMR (CDCl$_3$), δ (ppm); 1.20–1.90 (6H, m), 2.50–2.75 (2H, m), 3.10–4.00 (5H, m), 3.62 (2H, s), 4.91 (1H, d, J=5 Hz), 5.61 (½H, dd, J=5 Hz, 9 Hz), 5.62 (½H, dd, J=5 Hz, 9 Hz), 6.27 (½H, d, J=9 Hz), 6.37 (½H, d, J=9 Hz), 6.86 (1H, s), 7.10–7.50 (15H, m).

(b) Diphenylmethyl 7-amino-3-(tetrahydropyran-2-yl)methylthio-3-cephem-4-carboxylate Diphenylmethyl 7-phenylacetamido-3-(tetrahydropyran-2-yl)methylthio-3-cephem-4-carboxylate (1.60 g) was reacted in the same manner as in Example 11(b), yielding the titled compound in the form of hydrochloride (1.21 g; 87%).

NMR(DMSO-d$_6$), δ (ppm); 1.10–1.80 (6H, m), 2.99 (2H, d, J=6 Hz), 3.00–4.00 (5H, m), 5.02 (1H, d, J=5 Hz), 5.24 (1H, d, J=5 Hz), 6.83 (1H, s), 7.10–7.50 (10H, m).

(c) Diphenylmethyl 7-[(Z)-2-(2-tritylaminothiazol-4-yl)-2-methoxyiminoacetamido]-3-(tetrahydropyran-2-yl)methylthio-3-cephem-4-carboxylate Diphenylmethyl 7-amino-3-(tetrahydropyran-2-yl)methylthio-3-cephem-4-carboxylate hydrochloride (300 mg) was reacted with (Z)-2-(2-tritylaminothiazol-4-yl)-2-methoxyiminoacetic acid (267 mg), followed by purifying the reaction product in accordance with the procedure of Example 1(d), affording the titled compound (360 mg; 78%).

NMR(CDCl$_3$), δ (ppm); 1.20–1.90 (6H, m), 2.60–2.80 (2H, m), 3.10–4.00 (5H, m), 4.03 (3H, s), 5.02 (1H, d, J=5 Hz), 5.76 (1H, dd, J=5 Hz, 9 Hz), 6.73 (1H, s), 6.90 (1H, s), 7.10–7.50 (26H, m).

(d) 7-[(Z)-2-(2-aminothiazol-4-yl)-2-methoxyiminoacetamido]-3-(tetrahydropyran-2-yl)methylthio-3-cephem-4-carboxylic acid Diphenylmethyl 7-[(Z)-2-(2-tritylaminothiazol-4-yl)-2-methoxyiminoacetamido]-3-(tetrahydropyran-2-yl)methylthio-3-cephem-4-carboxylate (350 mg) was subjected to the reaction and subsequent purification as in the procedure of Example 1(e), affording the titled compound as sodium salt (130 mg; 63%).

NMR(D$_2$O), δ (ppm); 1.20–1.90 (6H, m), 2.79 (2H, d, J=8 Hz), 3.30–4.00 (5H, m), 4.00 (3H, s), 5.19 (1H, d, J=5 Hz), 5.75 (1H, d, J=5 Hz), 6.98 (1H, s).

EXAMPLE 24

Preparation of pivaloyloxymethyl 7-[(Z)-2-(2-aminothiazol-4-yl)-2-methoxyiminoacetamido]-3-(tetrahydropyran-2-yl)methylthio-3-cephem-4-carboxylate Sodium 7-[(Z)-2-(2-aminothiazol-4-yl)-2-methoxyiminoacetamido]-3-(tetrahydropyran-2-yl)methylthio-3-cephem-4-carboxylate (80 mg) was reacted with iodomethyl pivalate (72 mg), followed by purifying the reaction product in accordance with the procedure of Example 2, giving the titled compound (50 mg; 53%)

NMR(CDCl$_3$), δ (ppm); 1.21 (9H, s), 1.30–2.20 (6H, m), 2.70–2.90 (2H, m), 3.20–4.00 (5H, m), 4.03 (3H, s), 5.07 (1H, d, J=5 Hz), 5.10–5.80 (2H, br-s), 5.80 (1H, d, J=7 Hz), 5.82 (1H, dd, J=5 Hz, 9 Hz), 5.88 (1H, d, J=7 Hz), 6.84 (1H, s), 7.50 (1H, d, J=9 Hz).

EXAMPLE 25

Preparation of 7-[(Z)-(2-aminothiazol-4-yl)-2-hydroxyiminoacetamido]-3-(tetrahydropyran-2-yl) methylthio-3-cephem-4-carboxylic acid (a) Diphenylmethyl 7-[(Z)-2-(2-tritylaminothiazol-4-yl)-2-trityloxyiminoacetamido]-3-(tetrahydropyran-2-yl)methylthio-3-cephem-4-carboxylate Diphenylmethyl 7-amino-3-(tetrahydropyran-2-yl)methylthio-3-cephem-4-carboxylate hydrochloride (300 mg) was reacted with (Z)-2-(2-tritylaminothiazol-4-yl)-2-trityloxyiminoacetic acid (403 mg) in accordance with the procedure of Example 1(d). The crude reaction product was purified by a column chromatography on a silica gel column (30 g) with elution using benzene-ethyl acetate (7:1 by volume) as eluent to collect fractions containing the titled compound. Concentration of the fractions so collected gave the titled compound (380 mg; 60%).

NMR(CDCl₃), δ (ppm); 1.20–1.80 (6H, m), 2.50–2.80 (2H, m), 3.10–4.00 (5H, m), 5.03 (1H, d, J=5 Hz), 5.88 (1H, dd, J=5 Hz, 9 Hz), 6.41 (1H, s), 6.70 (1H, s), 6.93 (1H, s), 7.10–7.50 (41H, m).

(b) 7-[(Z)-2-(2-Aminothiazol-4-yl)-2-hydroxyiminoacetamido]-3-(tetrahydropyran-2-yl)methylthio-3-cephem-4-carboxylic acid Diphenylmethyl 7-[(Z)-2-(2-tritylaminothiazol-4-yl)-2-trityloxyiminoacetamido]-3-(tetrahydropyran-2-yl)methylthio-3-cephem-4-carboxylate (370 mg) was subjected to the reaction and subsequent purification as in the procedure of Example 3(b), yielding the titled compound (100 mg; 59%).

NMR(D₂O), δ (ppm); 1.20–1.90 (6H, m), 2.78 (2H, d, J=8 Hz), 3.30–4.00 (5H, m), 5.20 (1H, d, J=5 Hz), 5.75 (1H, d, J=5 Hz), 6.93 (1H, s).

EXAMPLE 26

Preparation of pivaloyloxymethyl 7-[(Z)-2-(2-aminothiazol-4-yl)-2-hydroxyiminoacetamido]-3-(tetrahydropyran-2-yl)methylthio-3-cephem-4-carboxylate Sodium 7-[(Z)-2-(2-aminothiazol-4-yl)-2-hydroxyiminoacetamido]-3-(tetrahydropyran-2-yl)methylthio-3-cephem-4-carboxylate (65 mg) was reacted with iodomethyl pivalate (46 mg) in accordance with the procedure of Example 4. The crude reaction product was purified by a column chromatography on a silica gel column (12 g) with elution using chloroform-methanol (10:1 by volume) as eluent to collect fractions containing the titled compound. The fractions so collected were concentrated to a small volume, to which was added diisopropylether dropwise and slowly, resulting in the deposition of crystals. The crystals were taken up by filtration, followed by washing with diisopropylether and drying, affording the titled compound (48 mg; 62%).

NMR (DMSO-d₆), δ (ppm); 1.23 (9H, s), 1.30–1.90 (6H, m), 2.70–2.90 (2H, m), 3.10–4.00 (5H, m), 5.07 (1H, d, J=5 Hz), 5.77 (1H, dd, J=5 Hz, 9 Hz), 5.80 (1H, d, J=8 Hz), 5.86 (1H, d, J=8 Hz), 6.00–6.20 (2H, br-s), 6.90 (1H, s), 9.94 (1H, d, J=9 Hz).

EXAMPLE 27

Preparation of 7-[(Z)-2-(2-aminothiazol-4-yl)-2-methoxyiminoacetamido]-3-(tetrahydrofuran-3-yl)methylthio-3-cephem-4-carboxylic acid (a) Tetrahydrofuran-3-ylmethyl trifluoromethanesulfonate Tetrahydrofuran-3-yl-methanol (177 mg) and pyridine (0.15 ml) were dissolved in dichloromethane (2 ml) and the solution was cooled to −60° C. Trifluoromethanesulfonic acid anhydride (537 mg) was added dropwise to the cooled solution, followed by stirring at −60° C. for 10 minutes, and the resulting reaction solution containing the titled trifluoromethanesulfonate as produced was washed with cold water and dried over anhydrous magnesium sulfate, after which the solvent was distilled off in vacuo until the solution was concentrated to a volume of about 1 ml.

(b) Diphenylmethyl 7-[(Z)-2-(2-tritylaminothiazol-4-yl)-2-methoxyiminoacetamido]-3-(tetrahydrofuran-3-yl)methylthio-3-cephem-4-carboxylate A first solution was prepared by dissolving diphenylmethyl 7-[(Z)-2-(2-tritylaminothiazol-4-yl)-2-methoxyiminoacetamido ]-3-acetylthio-3-cephem-4-carboxylate (500 mg) in hexamethylphosphoric triamide (5 ml), followed by ice-cooling the solution. A second solution was prepared by dissolving morpholine (0.87 ml) and triethylamine (1.39 ml) in benzene to give 10 ml of the second solution. The second solution (0.58 ml) was added dropwise to the first solution under ice-cooling and the resulting mixture was stirred under ice-cooling for 30 minutes. Then, the tetrahydrofuran-3-ylmethyl trifluoromethanesulfonate prepared in step (a) above was added to the above mixture and the resulting mixture was stirred for further 15 minutes. After adding cold water (10 ml) to the resulting reaction solution, the solution was extracted with ethyl acetate (10 ml). The organic layer as obtained from the extraction was washed once with water, dried over anhydrous magnesium sulfate and concentrated under reduced pressure to give an oil. The oil was purified by silica gel column chromatography with elution using toluene-ethyl acetate (3:1 by volume) as eluent to collect fractions containing the titled compound, and the fractions thus collected were concentrated to afford the titled compound (429 mg, 82%).

NMR (CDCl₃), δ (ppm); 1.56 (1H, m), 2.03 (1H, m), 2.28 (1H, m), 2.62 (2H, m), 3.20–3.90 (6H, m), 4.07 (3H, s), 5.07 (1H, d, J=5 Hz), 5.76 (1H, dd, J=5 Hz, 9 Hz), 6.78 (1H, S), 6.93 (1H, s), 7.20–7.50 (27H, m).

(c) 7-[(Z)-2-(2-Aminothiazol-4-yl)-2-methoxyiminoacetamido]-3-(tetrahydrofuran-3-yl)methylthio-3-cephem-4-carboxylic acid Diphenylmethyl 7-[(Z)-2-(2-tritylaminothiazol-4-yl)-2-methoxyiminoacetamido]-3-(tetrahydrofuran-3-yl)methylthio-3-cephem-4-carboxylate (417 mg) was dissolved in anisole (2 ml), to which trifluoroacetic acid (4 ml) was then added under ice-cooling, and the resulting mixture was allowed to stand under ice-cooling for 30 minutes to effect the deprotection reactions. Then, the reaction solution was added dropwise to diisopropylether (20 ml) under ice-cooling to cause precipitation. The precipitate was taken up by filtration and suspended in cold water (3 ml) and the suspension was neutralized with an aqueous sodium hydrogen carbonate up to pH 7–8. The resulting solution was purified by a column chromatography on a column of "Diaion HP-20" (100 ml) with elution using 5% aqueous acetone as eluent to collect fractions containing the titled compound. The fractions thus collected were concentrated to a small volume and lyophilized to afford the titled compound as sodium salt (114 mg; 48%).

NMR(DMSO-d₆), δ (ppm); 1.54 (1H, m), 2.02 (1H, m), 2.30 (1H, m), 2.60–2.80 (2H, m), 3.50–3.90 (9H, m), 5.00 (1H, d, J=5 Hz), 5.54 (1H, dd, J=5 Hz, 9 Hz), 6.81 (1H, s), 7.22 (2H, s), 9.55 (1H, d, J=9 Hz).

EXAMPLE 28

Preparation of pivaloyloxymethyl 7-[(Z)-2-(2-aminothiazol-4-yl)-2-methoxyiminoacetamido]-3-(tetrahydrofuran-3-yl)methylthio-3-cephem-4-carboxylate Sodium 7-[(Z)-2-(2-aminothiazol-4-yl)-2-methoxyiminoacetamido]-3-(tetrahydrofuran-3-yl)methylthio-3-cephem-4-carboxylate (71 mg) was dissolved in dimethylformamide (1 ml) and the solution was cooled to −20° C. The solution, after addition of iodomethyl pivalate (66 mg) thereto, was stirred at a temeprature of −20° to 10° C. for 30 minutes, after which cold water (10 ml) was added to the reaction solution. The resulting mixture was extracted with ethyl acetate (10 ml) and the organic layer separated was washed with an aqueous sodium chloride, dried over anhydrous magnesium sulfate and concentrated under reduced pressure to leave a yellow oil. The oily residue was purifed by a column chromatography on a silica gel column (40 g) with elution using ethyl acetate as eluent to collect fractions containing the titled compound. Concentration of the fractions so collected under reduced pressure gave the titled compound (77 mg; 92%).

NMR(CDCl$_3$), δ (ppm); 1.28 (9H, s), 1.68 (1H, m), 2.15 (1H, m), 2.42 (1H, m), 2.86 (2H, m), 3.50–3.90 (6H, m), 4.06 (3H, s), 5.15 (1H, d, J=5 Hz), 5.48 (2H, s), 5.88 (1H, d, J=6 Hz), 5.92 (1H, d, J=6 Hz), 5.97 (1H, dd, J=5 Hz, 9 Hz), 6.80 (1H, s), 7.95 (1H, d, J=9 Hz).

EXAMPLE 29

(a) Diphenylmethyl 7-[(Z)-2-(2-tritylaminothiazol-4-yl)-2-methoxyiminoacetamido]-3-(1,3-dioxolan-4-yl)methylthio-3-cephem-4-carboxylate 1,3-Dioxolan-4-ylmethyl trifluoromethanesulfonate was prepared in the same manner as in Example 27 (a) from 1,3-dioxolan-4-ylmethanol (180 mg), pyridine (0.15 ml) and trifluoromethanesulfonic acid anhydride (537 mg). On the other hand, diphenylmethyl 7-[(Z)-2-(2-tritylaminothiazol-4-yl)-2-methoxyiminoacetamido]-3-acetylthio-3-cephem-4-carboxylate (500 mg) was reacted with morpholine and triethylamine in the same manner as in Example 27 (b), followed by reacting the resulting reaction product with the 1,3-dioxolan-4-ylmethyl trifluoromethanesulfonate in the same manner as in Example 27 (b). The reaction solution so obtained was post-treated in the same manner as in Example 27 (b) and the produced compound was recovered and purified similarly to Example 27 (b) to afford the titled compound (494 mg; 94%).

NMR (CDCl$_3$), δ (ppm); 2.70–3.00 (2H, m), 3.50–4.10 (5H, m), 4.08 (3H, s), 4.81 (1H, s), 4.98 (½H, s), 5.00 (½H, s), 5.08 (1H, d, J=5 Hz), 5.86 (1H, dd, J=5 Hz, 9 Hz), 6.78 (1H, s), 6.96 (1H, s), 7.10–7.50 (27H, m).

(b) 7-[(Z)-2-(2-aminothiazol-4-yl)-2-methoxyiminoacetamido]-3-(1,3-dioxolan-4-yl)methylthio-3-cephem-4-carboxylic Acid Diphenylmethyl 7-[(Z)-2-(2-tritylaminothiazol-4-yl)-2-methoxyiminoacetamino]-3-(1,3-dioxolan-4-yl)methylthio-3-cephem-4-carboxylate (494 mg) prepared as above was treated with anisole and trifluoroacetic acid in the same manner as in Example 27(c) for the deprotection reactions, and the resulting reaction solution was post-treated and the produced compound was recovered and purified in the same manner as in Example 27(c) to afford a sodium salt of the titled compound (188 mg; 66%).

NMR (DMSO-d$_6$), δ (ppm); 2.60–3.00 (2H, m), 3.30–3.70 (3H, m), 3.87 (3H, s), 4.12 (2H, m), 4.77 (1H, s), 4.86 (½H, s), 4.89 (½H, s), 5.01 (1H, d, J=5 Hz), 5.67 (1H, dd, J=5 Hz, 9 Hz), 6.73 (1H, s), 7.15 (2H, s), 9.60 (1H, d, J=9 Hz).

EXAMPLE 30

Pivaloyloxymethyl 7-[(Z)-2-(2-aminothiazol-4-yl)-2-methoxyiminoacetamido]-3-(1,3-dioxolan-4-yl)methylthio-3-cephem-4-carboxylate Sodium 7-[(Z)-2-(2-aminothiazol-4-yl)-2-methoxyiminoacetamido]-3-(1,3-dioxolan-4-yl)methylthio-3-cephem-4-carboxylate (87 mg) as prepared in Example 29(b) was reacted with iodomethyl pivalate (80 mg) similarly to Example 28 for the esterification reaction. The resulting reaction solution was post-treated and the produced compound was recovered and purified similarly to Example 28 to give the titled compound (86 mg; 84%).

NMR (CDCl$_3$), δ (ppm); 1.23 (9H, s), 2.80–3.10 (2H, m), 3.60–3.80 (3H, m), 4.00–4.30 (2H, m), 4.07 (3H, s), 4.84 (½H, s), 4.85 (½H, s), 5.01 (½H, s), 5.04 (½H, s), 5.14 (1H, d, J=5 Hz), 5.45 (2H, s), 5.88 (1H, d, J=6 Hz), 5.92 (1H, m), 5.97 (1H, dd, J=5 Hz, 9 Hz), 6.83 (1H, s), 7.77 (1H, d, J=9 Hz), 7.79 (1H, d, J=9 Hz).

EXAMPLE 31

(a) Diphenylmethyl 7-[(Z)-2-(2-tritylaminothiazol-4-yl)-2-methoxyiminoacetamido]-3-(tetrahydropyran-4-yl)methylthio-3-cephem-4-carboxylate Tetrahydropyran-4-ylmethyl trifluoromethanesulfonate was prepared in the same manner as in Example 27(a) from tetrahydropyran-4-yl-methanol (348 mg), pyridine (0.27 ml) and trifluoromethanesulfonic acid anhydride (931 mg). On the other hand, diphenylmethyl 7-[(Z)-2-(2-tritylaminothiazol-4-yl)-2-methoxyiminoacetamido]-3-acetylthio-3-cephem-4-carboxylate (866 mg) was reacted with morpholine and triethylamine in the same manner as in Example 27(b), followed by reacting the resulting reaction product with the tetrahydropyran-4-ylmethyl trifluoromethanesulfonate in the same manner as in Example 27(b). The reaction solution so obtained was post-treated in the same manner as in Example 27(b) and the produced compound was recovered and purified similarly to Example 27 (b) to afford the titled compound (904 mg; 98%).

NMR (CDCl$_3$), δ (ppm); 1.20–2.00 (5H, m), 2.54 (2H, d, J=6 Hz), 3.20–3.50 (4H, m), 3.90–4.00 (2H, m), 4.07 (3H, s), 5.08 (1H, d, J=5 Hz), 5.77 (1H, dd, J=5 Hz, 9 Hz), 6.78 (1H, s), 6.93 (1H, s), 7.20–7.50 (27H, m).

(b) 7-[(Z)-2-(2-aminothiazol-4-yl)-2-methoxyiminoacetamido]-3-(tetrahydropyran-4-yl)methylthio-3-cephem-4-carboxylic acid Diphenylmethyl 7-[(Z)-2-(2-tritylaminothiazol-4-yl)-2-methoxyiminoacetamino]-3-(tetrahydropyran-4-yl)methylthio-3-cephem-4-carboxylate (904 mg) prepared as above was treated with anisole and trifluoroacetic acid in the same manner as in Example 27(c) for the deprotection reactions, and the resulting reaction solution was post-treated and the produced compound was recovered and purified in the same manner as in Example 27(c) to afford a sodium salt of the titled compound (310 mg; 59%).

NMR(DMSO-$d_6$), δ (ppm); 1.16 (2H, m), 1.63 (1H, m), 1.74 (2H, m), 2.56 (2H, d, J=6 Hz), 3.20–3.40 (3H, m), 3.62 (1H, d, J=7 Hz), 3.82 (2H, m), 3.86 (3H, s), 4.99 (1H, d, J=5 Hz), 5.53 (1H, dd, J=5 Hz, 9 Hz), 6.73 (1H, s), 7.16 (2H, s), 9.55 (1H, d, J=9 Hz).

EXAMPLE 32

Pivaloyloxymethyl 7-[(Z)-2-(2-aminothiazol-4-yl)-2-methoxyiminoacetamido]-3-(tetrahydropyran-4-yl)methylthio-3-cephem-4-carboxylate Sodium 7-[(Z)-2-(2-aminothiazol-4-yl)-2-methoxyiminoacetamido]-3-(tetrahydropyran-4-yl)methylthio-3-cephem-4-carboxylate (200 mg) as prepared in Example 31(b) was reacted with iodomethyl pivalate (181 mg) similarly to Example 28 for the esterification reaction. The resulting reaction solution was post-treated and the produced compound was recovered and purified similarly to Example 28 to give the titled compound (120 mg; 51%).

NMR (CDCl$_3$) δ (ppm); 1.22 (9H, s), 1.30–2.00 (5H, m), 2.73 (2H, m), 3.34 (2H, m), 3.56 (1H, d, J=7 Hz), 3.63 (1H, d, J=7 Hz), 3.95 (2H, m), 4.05 (3H, s), 5.16 (1H, d, J=5 Hz), 5.72 (2H, s), 5.86 (1H, d, J=6 Hz), 5.91 (1H, m), 5.98 (1H, dd, J=5 Hz, 9 Hz), 6.72 (1H, s), 8.33 (1H, d, J=9 Hz).

EXAMPLE 33

(a) Diphenylmethyl 7-[(Z)-2-(2-tritylaminothiazol-4-yl)-2-methoxyiminoacetamido]-3-(1,3-dioxan-5-yl)methylthio-3-cephem-4-carboxylate 1,3-Dioxan-5-ylmethyl trifluoromethanesulfonate was prepared in the same manner as in Example 27 (a) from 1,3-dioxan-5-ylmethanol (205 mg), pyridine (0.15 ml) and trifluoromethanesulfonic acid anhydride (5.39 mg). On the other hand, diphenylmethyl 7-[(Z)-2-(2-tritylaminothiazol-4-yl) -2-methoxyiminoacetamido]-3-acetylthio-3-cephem-4-carboxylate (500 mg) was reacted with morpholine and triethylamine in the same manner as in Example 27 (b), followed by reacting the resulting reaction product with the 1,3-dioxan-4-ylmethyl trifluoromethanesulfonate in the same manner as in Example 27 (b). The reaction solution so obtained was post-treated in the same manner as in Example 27 (b) and the produced compound was recovered and purified similarly to Example 27 (b) to afford the titled compound (490 mg; 92%).

NMR (CDCl$_3$), δ (ppm); 1.73 (1H, m), 2.87 (2H, m), 3.45–3.70 (4H, m), 3.89 (2H, m), 4.08 (3H, s), 4.78 (2H, ABq), 5.08 (1H, d, J=5 Hz), 5.83 (1H, dd, J=5 Hz, 9 Hz), 6.78 (1H, s), 6.93 (1H, s), 7.20–7.50 (27H, m).

(b) 7-[(Z)-2-(2-aminothiazol-4-yl)-2-methoxyiminoacetamido]-3-(1,3-dioxan-5-yl)methylthio-3-cephem-4-carboxylic Acid Diphenylmethyl 7-[(Z)-2-(2-tritylaminothiazol-4-yl)-2-methoxyiminoacetamido]-3-(1,3-dioxan-5-yl)methylthio-3-cephem-4-carboxylate (490 mg) prepared as above was treated with anisole and trifluoroacetic acid in the same manner as in Example 27(c) for the deprotection reactions, and the resulting reaction solution was post-treated and the produced compound was recovered and purified in the same manner as in Example 27(c) to afford a sodium salt of the titled compound (193 mg; 68%).

NMR (DMSO-$d_6$), δ (ppm); 1.75 (1H, m), 2.80 (2H, m), 3.20–3.70 (6H, m), 3.86 (3H, s), 4.80 (2H, ABq), 4.99 (1H, d, J=5 Hz), 5.53 (1H, dd, J=5 Hz, 9 Hz), 6.73 (1H, s), 7.16 (2H, s), 9.55 (1H, d, J=9 Hz).

EXAMPLE 34

Pivaloyloxymethyl 7,[(Z)-2-(2-aminothiazol-4-yl)-2-methoxyiminoacetamido]-3-(1,3-dioxan-5-yl)methylthio-3-cephem-4-carboxylate Sodium 7-[(Z)-2-(2-aminothiazol-4-yl)-2-methoxyiminoacetamido]-3-(1,3-dioxan-5-yl)methylthio-3-cephem-4-carboxylate (152 mg) as prepared in Example 33(b) was reacted with iodomethyl pivalate (80 mg) similarly to Example 28 for the esterification reaction. The resulting reaction solution was post-treated and the produced compound was recovered and purified similarly to Example 28 to give the titled compound (94 mg; 53%).

NMR(CDCl$_3$), δ (ppm); 1.25 (9H, s), 1.78 (1H, m), 3.00 (2H, m), 3.65 (2H, s), 3.79 (2H, m), 3.96 (2H, m), 4.05 (3H, s), 4.82 (2H, ABq), 5.05 (1H, d, J=5 Hz), 5.63 (2H, s), 5.87 (1H, d, J=6 Hz), 5.93 (1H, d, J=6 Hz), 5.98 (1H, dd, J=5 Hz, 9 Hz), 6.74 (1H, s), 8.15 (1H, d, J=9 Hz).

EXAMPLE 35

(a) Diphenylmethyl 7-[(Z)-2-(2-tritylaminothiazol-4-yl)-2-trityloxyiminoacetamido]-3-(1,3-dioxolan-4-yl)methylthio-3-cephem-4-carboxylate 1,3-Dioxolan-4-ylmethyl trifluoromethanesulfonate was prepared in the same manner as in Example 27(a) from 1,3-dioxolan-4-yl-methanol (200 mg), pyridine (0.17 ml) and trifluoromethanesulfonic acid anhydride (596 mg). On the other hand, diphenylmethyl 7-[(Z)-2-(2-tritylaminothiazol-4-yl)-2-trityloxyiminoacetamido]-3-acetylthio-3-cephem-4-carboxylate (700 mg) was reacted with morpholine and triethylamine in the same manner as in Example 27(b), followed by reacting the resulting reaction product with the 1,3-dioxolan-4-ylmethyl trifluoromethanesulfonate in the same manner as in Example 27(b). The reaction solution so obtained was post-treated in the same manner as in Example 27(b) and the produced compound was recovered and purified similarly to Example 27(b) to afford the titled compound (728 mg; 100%).

NMR (CDCl$_3$), δ (ppm); 2.82 (2H, m), 3.20–3.70 (3H, m), 4.10 (2H, m), 4.79 (1H, s), 4.87 (1H, s), 5.08 (1H, d, J=5 Hz), 5.93 (1H, dd, J=5 Hz, 9 Hz), 6.47 (1H, s), 6.75 (1H, s), 6.95 (1H, s), 7.20–7.50 (41H, m).

(b) 7-[(Z)-2-(2-aminothiazol-4-yl)-2-hydroxyiminoacetamido]-3-(1,3-dioxolan-4-yl)methylthio-3-cephem-4-carboxylic acid Diphenylmethyl 7-[(Z)-2-(2-tritylaminothiazol-4-yl)-2-trityloxyiminoacetamido]-3-(1,3-dioxolan-4-yl)methylthio-3-cephem-4-carboxylate (728 mg) prepared as above was treated with anisole and trifluoroacetic acid in the same manner as in Example 27(c) for the deprotection reactions, and the resulting reaction solution was post-treated and the produced compound was recovered and purified in the same manner as in Example 27(c) to afford a sodium salt of the titled compound (166 mg; 50%).

NMR (DMSO-d₆), δ (ppm); 2.65 (1H, m), 2.95 (1H, m), 3.20–3.70 (3H, m), 4.10 (2H, m), 4.78 (1H, s), 4.87 (½H, s), 4.88 (½H, s), 5.01 (1H, d, J=5 Hz), 5.55 (1H, dd, J=5 Hz, 9 Hz), 6.66 (1H, s), 7.13 (2H, s), 9.42 (1H, d, J=9 Hz), 11.28 (1H, s).

EXAMPLE 36

Pivaloyloxymethyl 7-[(Z)-2-(2-aminothiazol-4-yl)-2-hydroxyiminoacetamido]-3-(1,3-dioxolan-4-yl)methylthio-3-cephem-4-carboxylate Sodium 7-[(Z)-2-(2-aminothiazol-4-yl)-2-trityloxyiminoacetamido]-3-(1,3-dioxolan-4-yl)methylthio-3-cephem-4-carboxylate (71 mg) as prepared in Example 35(b) was reacted with iodomethyl pivalate (68 mg) similarly to Example 28 for the esterification reaction. The resulting reaction solution was post-treated and the produced compound was recovered and purified similarly to Example 28 to give the titled compound (43 mg; 51%).

NMR(CDCl₃), δ (ppm); 1.22 (9H, s). 3.00 (2H, m), 3.50–4.30 (5H, m), 4.84 (1H, s), 5.01 (½H, s), 5.03 (½H, s), 5.10 (1H, d, J=5 Hz), 5.58 (2H, s), 5.82 (1H, dd, J=5 Hz, 9 Hz), 5.87 (1H, d, J=6 Hz), 5.92 (1H, d, J=6 Hz), 7.00 (1H, s), 10.59 (1H, s).

EXAMPLE 37

(a) Diphenylmethyl 7-[(Z)-2-(2-tritylaminothiazol-4-yl)-2-trityloxyiminoacetamido]-3-(tetrahydropyran-4-yl)methylthio-3-cephem-4-carboxylate Tetrahydropyran-4-ylmethyl · trifluoromethanesulfonate was prepared in the same manner as in Example 27 (a) from tetrahydropyran-4-yl-methanol (223 mg), pyridine (0.17 ml) and trifluoromethanesulfonic acid anhydride (596 mg). On the other hand, diphenylmethyl 7-[(Z)-2-(2-tritylaminothiazol-4 -yl) -2 -trityloxyiminoacetamido]-3-acetylthio-3-cephem-4-carboxylate (700 mg) was reacted with morpholine and triethylamine in the same manner as in Example 27(b), followed by reacting the resulting reaction product with the tetrahydropyran-4-ylmethyl trifluoromethanesulfonate in the same manner as in Example 27 (b).The reaction solution so obtained was post-treated in the same manner as in Example 27 (b) and the produced compound was recovered and purified similarly to Example 27 (b) to afford the titled compound (722 mg; 98%).

NMR (CEDl₃), δ (ppm); 1.20–2.00 (5H, m), 2.58 (2H, m), 3.20–3.50 (4H, m), 3.90–4.00 (2H, m), 5.10 (1H, d, J=5 Hz), 5.94 (1H, dd, J=5 Hz, 9 Hz), 6.45 (1H, s), 6.75 (1H, s), 6.96 (1H, s), 7.20–7.50 (41H, m).

(b) 7-[(Z)-2-(2-aminothiazol-4-yl)-2-hydroxyiminoacetamido]-3-(tetrahydropyran-4-yl)methylthio-3-cephem-4-carboxylic acid Diphenylmethyl 7-[(Z)-2-(2-tritylaminothiazol-4-yl)-2-trityloxyiminoacetamido]-3-(tetrahydropyran-4-yl)methylthio-3-cephem-4-carboxylate (722 mg) prepared as above was treated with anisole and trifluoroacetic acid in the same manner as in Example 27(c) for the deprotection reactions, and the resulting reaction solution was post-treated and the produced compound was recovered and purified in the same manner as in Example 27(c) to afford a sodium salt of the titled compound (192 mg; 53%).

NMR (DMSO-d₆), δ (ppm); 1.16 (2H, m), 1.63 (1H, m), 1.77 (2H, m), 2.56 (2H, d, J=6 Hz), 3.20–3.80 (6H, m), 5.01 (1H, d, J=5 hz), 5.52 (1H, dd, J=5 Hz, 9 Hz), 6.75 (1H, s), 7.15 (2H, s), 9.52 (1H, d, J=9 Hz), 11.22 (1H, s).

EXAMPLE 38

Pivaloyloxymethyl 7-[(Z)-2-(2-aminothiazol-4-yl)-2-hydroxyiminoacetamido3-3-(tetrahydropyran-4-yl)methylthio-3-cephem-4-carboxylate Sodium 7-[(Z)-2-(2-aminothiazol-4-yl)-2-hydroxyiminoacetamido]-3-(tetrahydropyran-4-yl)methylthio-3-cephem-4-carboxylate (132 mg) as prepared in Example 37(b) was reacted with iodomethyl pivalate (124 mg) similarly to Example 28 for the esterification reaction. The resulting reaction solution was post-treated and the produced compound was recovered and purified similarly to Example 28 to give the titled compound (48 mg; 51%).

NMR(CDCl₃), δ (ppm); 1.10–1.30 (11H, s), 1.60–1.80 (3H, m), 2.34 (2H, d, j=6 Hz), 3.30–4.00 (6H, m), 5.01 (1H, d, j=5Hz), 5.30 (2 H, s), 5.80 (1 H, dd, J=5 Hz, 9 Hz), 5.88 (1 H, d, J=6 Hz), 5.96 (1 H, d, J=6 Hz), 7.07 (1 H, s), 10.60 (1 H, s).

We claim:

1. A cephalosporin derivative of formula (I):

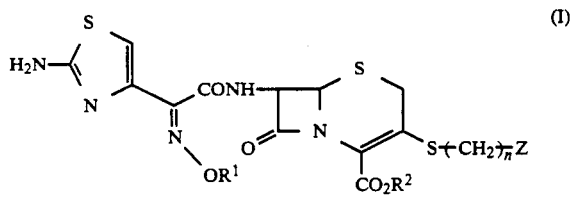

wherein $R^1$ is a hydrogen atom or a lower alkyl group, $R^2$ is a hydrogen atom or an ester-forming group capable of being cleaved easily with an esterase existing in the digestive tracts; n is an integer of zero or 1; Z is a tetrahydrofuranyl, tetrahydropyranyl, 1,3-dioxolanyl or 1,3-dioxanyl group which may be substituted by one or more lower alkyl groups, or a pharmaceutically acceptable salt thereof.

2. A cephalosporin derivative as claimed in claim 1 wherein Z is a tetrahydrofuranyl, tetrahydropyranyl, 1,3-dioxolanyl or 1,3-dioxanyl group which may be substituted by one or more lower alkyl groups.

3. A cephalosporin derivative as claimed in claim 2 wherein $R^1$ is a hydrogen atom or methyl group; n is 0 or 1; and Z is selected from the group consisting of tetrahydrofuran-2-yl, tetrahydrofuran-3-yl, tetrahydropyran-2-yl, tetrahydropyran-4-yl, 1,3-dioxolan-4-yl, 2,2-dimethyl-1,3-dioxolan-4-yl, 1,3-dioxan-5-yl and 2,2-dimethyl-1,3-dioxan-4-yl groups.

4. A cephalosporin derivative as claimed in claim 1 which is selected from the group consisting of: 7-[(Z)-2-(2-aminothiazol-4-yl)-2-methoxyiminoacetamido]-3-(tetrahydrofuran-3-yl)thio-3-cephem-4-carboxylic acid; its sodium salt (carboxylate) and its pivaloyloxymethyl ester, 7-[(Z)-2-(2-aminothiazol-4-yl)-2-methoxyiminoacetamido]-3-(tetrahydrofuran-3-yl)methylthio-3-cephem-4-carboxylic acid; its sodium salt (carboxylate) and its pivaloyloxymethyl ester, and 7-[(Z)-2-(2-aminothiazol-4-yl)-2-methoxyiminoacetamido]-3-(1,3-dioxolan-4-yl) methylthio-3-cephem-4-carboxylic acid;

its sodium salt (carboxylate) and its pivaloyloxymethyl ester.

5. A pharmaceutical, antibacterial composition comprising an antibacterially effective amount of a cephalosporin derivative of formula (I) as defined in claim 1 or a pharmaceutically acceptable salt thereof as active ingredient, in combination with a pharmaceutically acceptable carrier for the active ingredient.

* * * * *